United States Patent [19]

Hayashi et al.

[11] Patent Number: 5,098,599
[45] Date of Patent: Mar. 24, 1992

[54] OPTICALLY ACTIVE COMPOUND AND LIQUID CRYSTAL COMPOSITION

[75] Inventors: Seiji Hayashi, Kawasaki; Jun Nakauchi, Tokyo; Keiichi Sakashita, Akishima; Yoshitaka Kageyama, Tokyo; Yoshihiko Sako, Tokyo, all of Japan

[73] Assignee: Mitsubishi Rayon Company Ltd., Tokyo, Japan

[21] Appl. No.: 758,217

[22] Filed: Sep. 12, 1991

Related U.S. Application Data

[62] Division of Ser. No. 377,050, Jul. 7, 1989, abandoned.

[30] Foreign Application Priority Data

Jul. 8, 1988 [JP] Japan ................... 63-170146
Nov. 14, 1988 [JP] Japan ................... 63-287461

[51] Int. Cl.$^5$ ............... C09K 19/34; C09K 19/20; C09K 19/12
[52] U.S. Cl. ............... 252/299.61; 252/299.64; 252/299.66
[58] Field of Search ............... 252/299.01, 299.61, 252/299.66, 299.64

[56] References Cited

FOREIGN PATENT DOCUMENTS 0025119 3/1981 European Pat. Off.
0250087 12/1987 European Pat. Off.
3515374 6/1986 Fed. Rep. of Germany.
8705018 8/1987 World Int. Prop. O. ...... 252/299.61

*Primary Examiner*—John S. Maples
*Assistant Examiner*—Philip Tucker
*Attorney, Agent, or Firm*—Oblon, Spivak, McClelland, Maier & Neustadt

[57] ABSTRACT

Disclosed is an optically active compound represented by the formula:

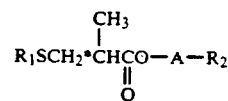

wherein A stands for (Abstract continued on next page.)

-continued

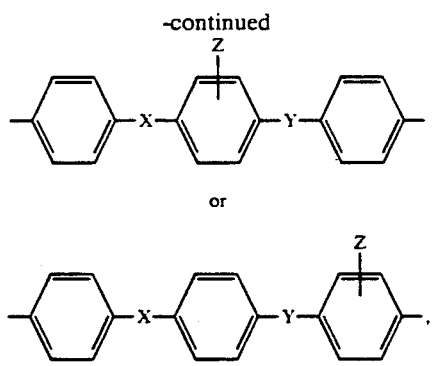

-continued

X and Y independently stand for $-\overset{O}{\underset{\|}{OC}}-$, $-\overset{O}{\underset{\|}{OC}}-$ or a single bond, Z stands for a hydrogen atom, a halogen atom or a cyano group, $R_1$ stands for an alkyl group or fluoroalkyl group having 1 to 18 carbon atoms, $R_2$ stands for an alkyl group or alkoxy group having 1 to 18 carbon atoms, and *C stands for the asymmetric carbon atom. This compound is used as a ferroelectric liquid crystal or an additive to a ferroelectric liquid crystal.

1 Claim, 15 Drawing Sheets

OPTICALLY ACTIVE COMPOUND AND LIQUID CRYSTAL COMPOSITION

This is a division of application Ser. No. 377,050, filed Jul. 7, 1989, now abandoned.

BACKGROUND OF THE INVENTION

(1) Field of the Invention

The present invention relates to a mesomorphic compound not disclosed in any literature reference, which is valuable as a ferroelectric liquid crystal or an additive to a ferroelectric liquid crystal, and to a liquid crystal composition comprising this optically active compound.

(2) Description of the Related Art

The liquid crystals currently widely used in a liquid crystal display (LCD) are classified into the nematic phase, and since they are of the light-receiving type, the display system using these liquid crystals is characterized in that there is no eye fatigue therefrom and the power consumption is very low. Nevertheless, the display system using these liquid crystals has problems in that the response speed is low and the view angle of the display is narrow.

A display device or printer head using a ferroelectric liquid crystal having advantageous characteristics similar to those of a nematic liquid crystal and having a high response speed and high contrast comparable to those of a light-emitting type display element has been investigated.

The ferroelectric liquid crystal was reported of its discovery for the first time by R.B. Meyer et al in 1975 [J. physique, 36, L-69 (1975)]. This ferroelectric liquid crystal is classified into the chiral smectic C phase (hereinafter referred to as "Sm*C phase"), and a typical compound of this ferroelectric liquid crystal is p-decyloxybenzylidene-p'-amino-2-methylbutyl cinnamate (hereinafter referred to as "DOBAMBC") represented by the following formula:

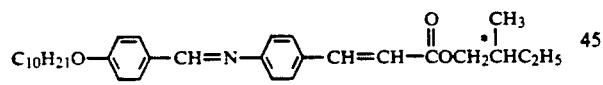

DOBAMBC and most of the ferroelectric liquid crystal materials proposed thereafter, have problems in that the temperature range showing the ferroelectricity (the temperature range in which the Sm*C phase is present) is narrow, and they cannot be used practically without an additive. Accordingly, attempts have been made to expand the temperature range showing the Sm*C phase of the lower and higher temperature sides, taking room temperature as the center, by mixing ferroelectric liquid crystals. Under this circumstance, the development of a ferroelectric liquid crystal showing the Sm*C phase in the practical temperature range is desired. Furthermore, the development of a ferroelectric liquid crystal having a larger spontaneous polarization than those of the known ferroelectric liquid crystals is desired in the field of printer heads for which an ultra-high response speed is required.

A compound having a Schiff base, such as DOBAMBC, has a poor light stability and is readily colored.

SUMMARY OF THE INVENTION

Therefore, a primary object of the present invention is to provide a ferroelectric liquid crystal which is chemically stable and is not colored and has an excellent light stability and a large spontaneous polarization, and a mesomorphic compound which gives a large spontaneous polarization to a liquid crystal composition when incorporated in the liquid crystal composition.

Another object of the present invention is to provide a liquid crystal composition comprising this optically active compound.

In accordance with the present invention, there is provided a mesomorphic compound represented by the following general formula (1):

$$R_1SCH_2\overset{*}{C}H\underset{O}{\overset{CH_3}{\underset{\|}{C}}}CO-A-R_2 \quad (1)$$

wherein A stands for 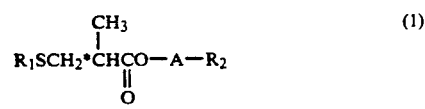,

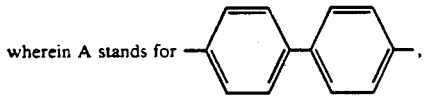

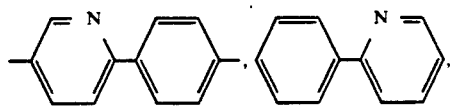

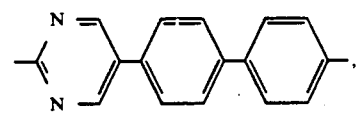

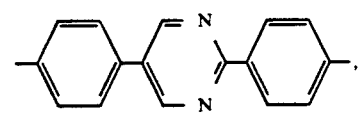

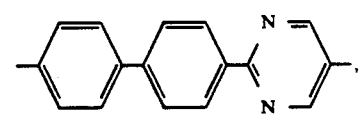

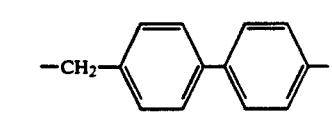

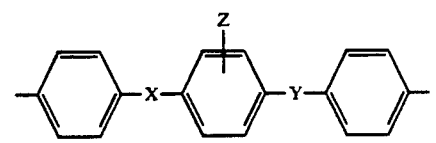

or

-continued

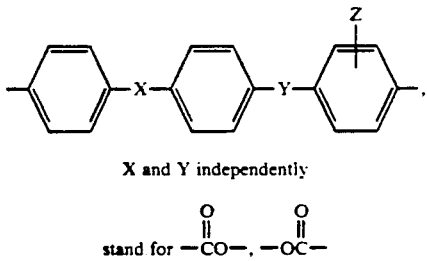

X and Y independently stand for $-\overset{O}{\underset{\|}{C}}O-$, $-O\overset{O}{\underset{\|}{C}}-$ or a single bond, Z stands for a hydrogen atom, a halogen atom or a cyano group, $R_1$ stands for an alkyl group or fluoroalkyl group having 1 to 18 carbon atoms, $R_2$ stands for an alkyl group or alkoxy group having 1 to 18 carbon atoms, and *C stands for the asymmetric carbon atom.

In accordance with the present invention, there is further provided a liquid crystal composition comprising at least one compound represented by the above formula (1).

DESCRIPTION OF THE PREFERRED EMBODIMENTS

Figure 1:
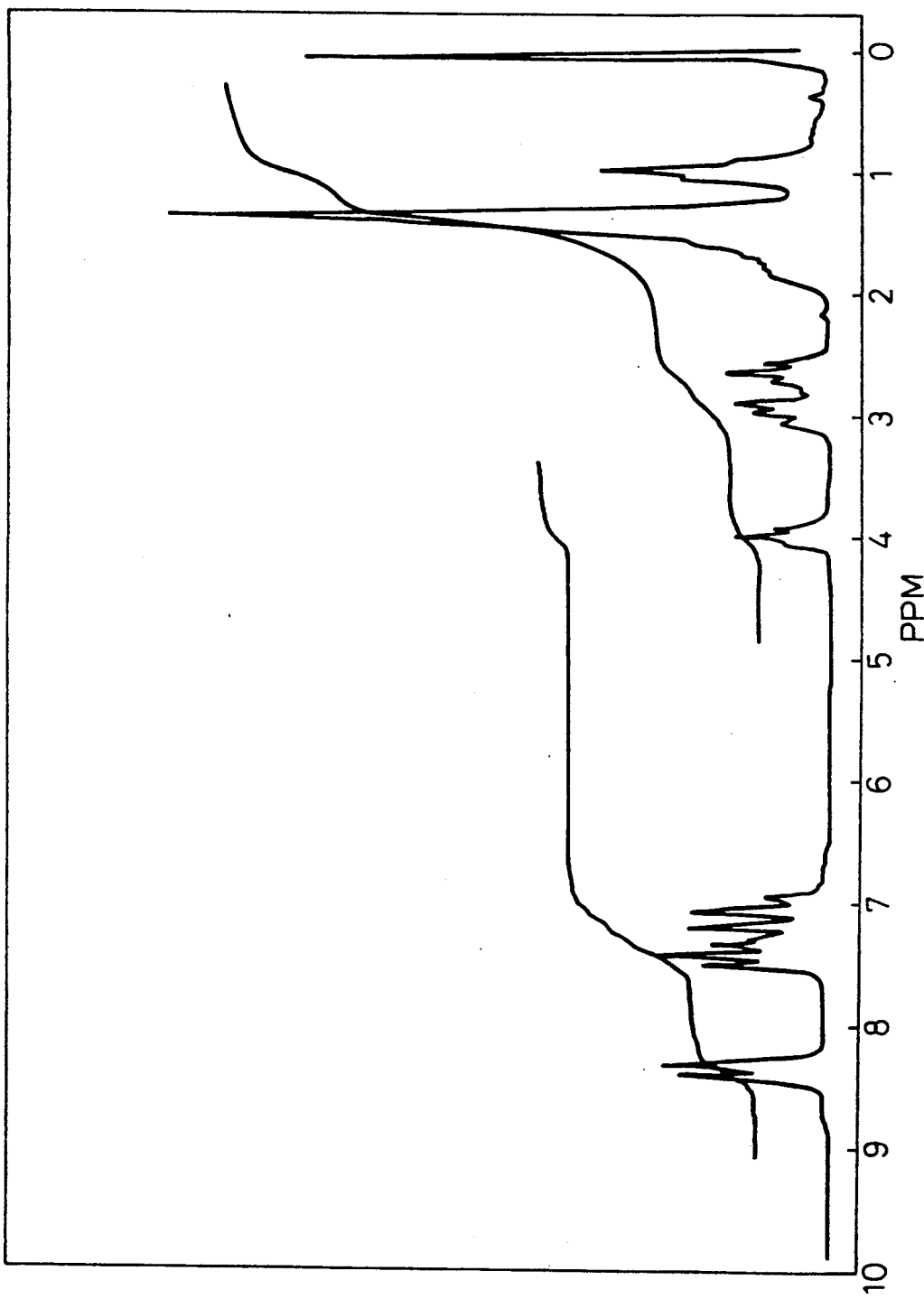
FIGS. 1 through 13 illustrates NMR spectra of optically active compounds prepared in Examples 1 through 13, respectively.

Of the compounds of the present invention, a compound containing a halogen atom or a cyano group in -A- has a broad temperature range showing the Sm*C phase and has a lower melting point than that of the corresponding compound free of a halogen atom or cyano group. It is sufficient if the carbon number of the alkyl, fluoroalkyl or alkoxy group represented by $R_1$ or $R_2$ is capable of stabilizing the Sm*C phase. If this carbon number is 1 to 18, the compounds of the present invention show good characteristics, and in view of the liquid crystal characteristic and the performance as the liquid crystal additive preferably the carbon number of $R_1$ is 1 to 12 and the carbon number of $R_2$ is 3 to 12. If each of the carbon numbers of $R_1$ and $R_2$ is 19 or larger, purification of the alkyl bromide used for the synthesis is relatively difficult and the productivity is reduced, and the spontaneous polarization is lowered.

The compounds represented by the general formula (1) can be synthesized through the following routes.

A) Preparation of optically active 3-alkylthio-2-methyl-propionic acid

An optically active 3-alkylthio-2-methylpropionic acid is synthesized by using D-(−)-β-acetylthio-α-methylpropionic acid or methyl L-(+)-β-acetylthio-α-methylpropionate as the starting material. The synthesis process using methyl L-(+)-β-acetylthio-α-methylpropionate will now be described. Note, an optically active 3-alkylthio-2-methylpropionic acid can be similarly synthesized when D-(−)-β-acetylthio-α-methylpropionic acid is used. The synthesis process using methyl L-(+)-β-acethylthio-α-methylpropionate is represented by the following reaction formula:

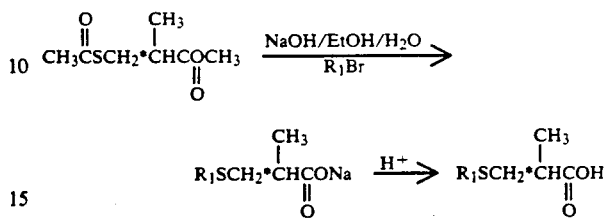

More specifically, sodium hydroxide is dissolved in water, an equal amount of ethanol is added to the aqueous solution, methyl L-(+)-β-acetylthio-α-methylpropionate is added to the mixture, stirring is conducted at room temperature for 1 hour, and an alkyl bromide is added to the mixture to effect reaction. Then the reaction liquid is made weakly acidic by an addition of hydrochloric acid and is extracted with ether, and the extract is washed three times with dilute hydrochloric acid and water in this order and dried with anhydrous magnesium sulfate. Evaporation of the solvent gives an optically active 3-alkylthio-2-methyl-propionic acid.

Also where $R_1$ is a fluoroalkyl group, an optically active 3-fluoroalkylthio-2-methylpropionic acid can be similarly synthesized by using a fluoroalkyl bromide instead of the alkyl bromide.

B) Preparation of compound represented by general formula (1)

The compound represented by the general formula (1) can be prepared, for example, through the following reaction:

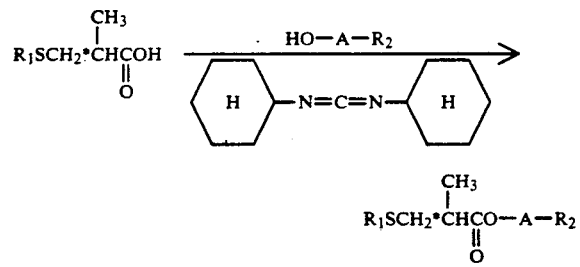

wherein A, $R_1$ and $R_2$ are as defined above.

The process for the synthesis of a compound of the general formula (1) will now be more specifically described.

The case wherein Z is a hydrogen atom will now be described. Compounds in which Z is a halogen atom or a cyano group can be similarly synthesized by using a starting compound having the substituent at the predetermined position.

B-1) Where each of X and Y in formula (1) is $-\overset{O}{\underset{\|}{C}}O-$

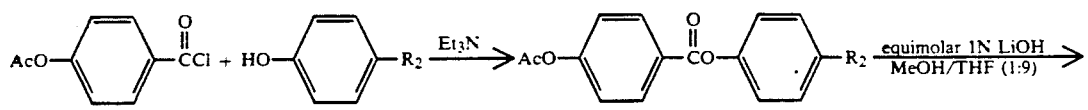
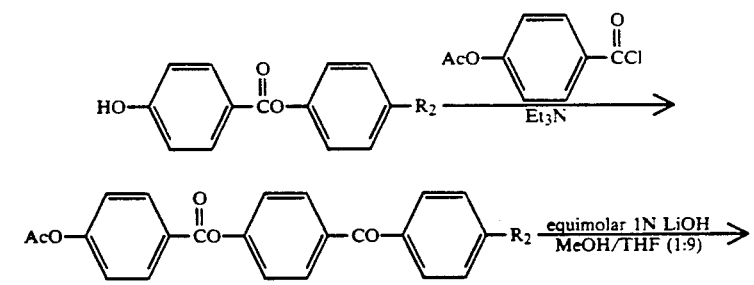
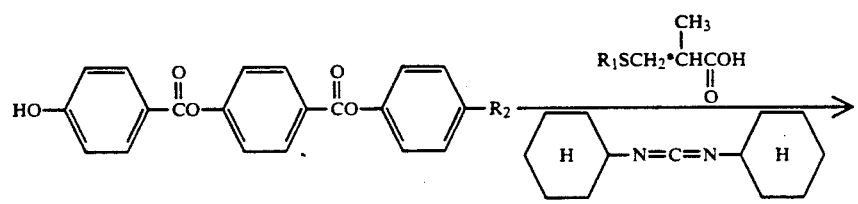
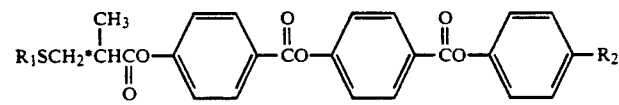
B-2) Where X is —$\overset{O}{\overset{\|}{C}}$O— and Y is —O$\overset{O}{\overset{\|}{C}}$— in general formula (1)
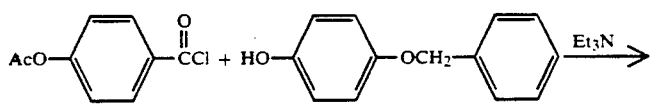
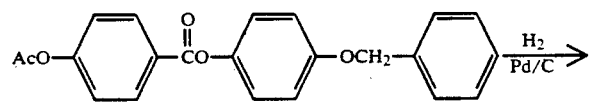
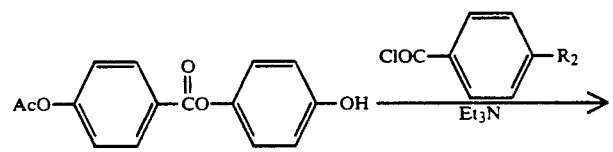
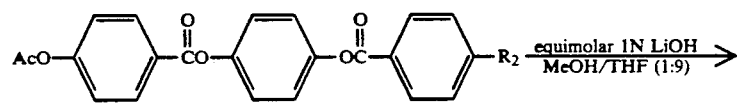
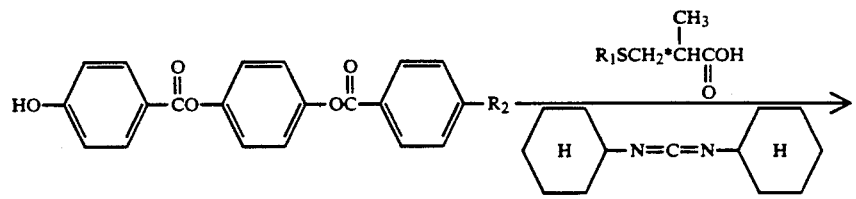
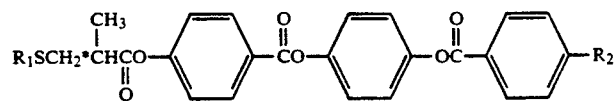

-continued
B-3) Where X is —CO— and Y is a single bond in general formula (1)
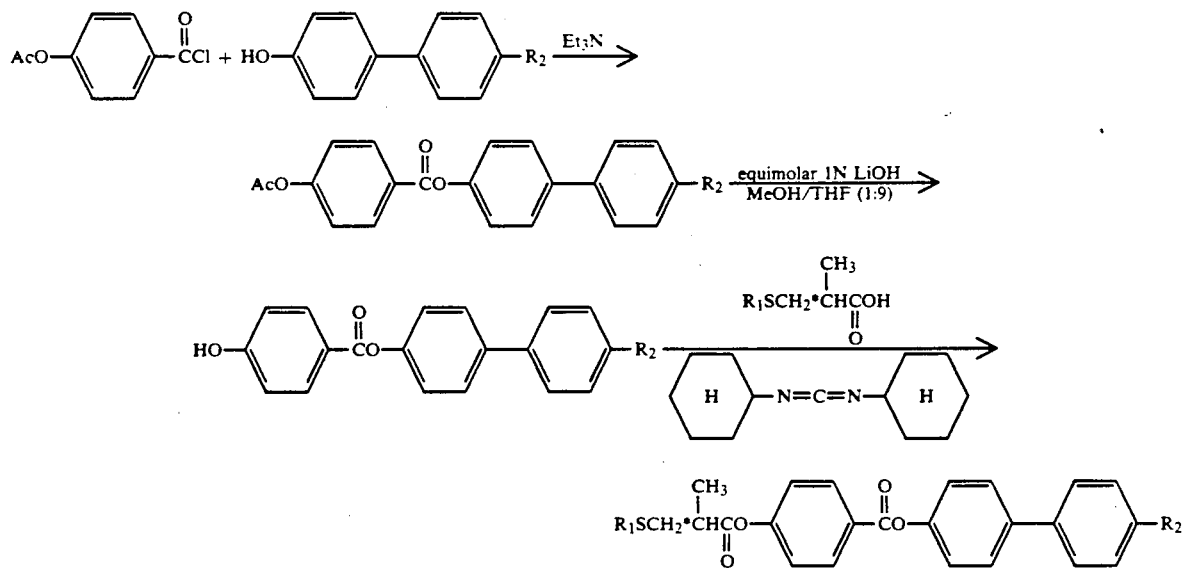
B-4) Where X is —OC— and Y is —CO— in general formula (1)
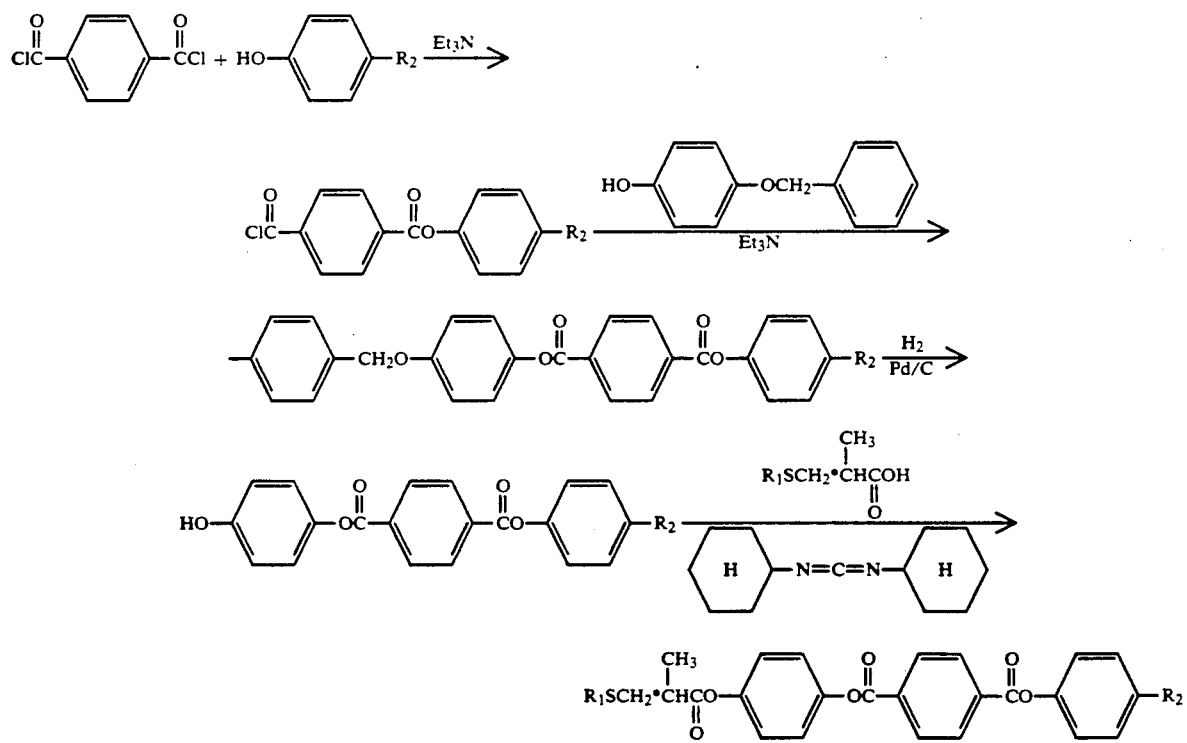
B-5) Where each of X and Y in general formula (1) is —OC—
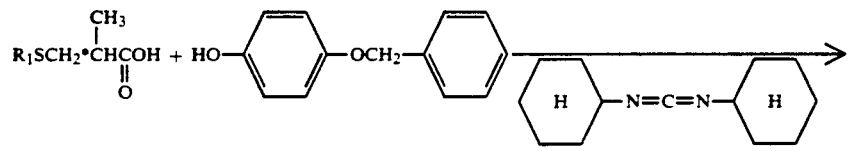

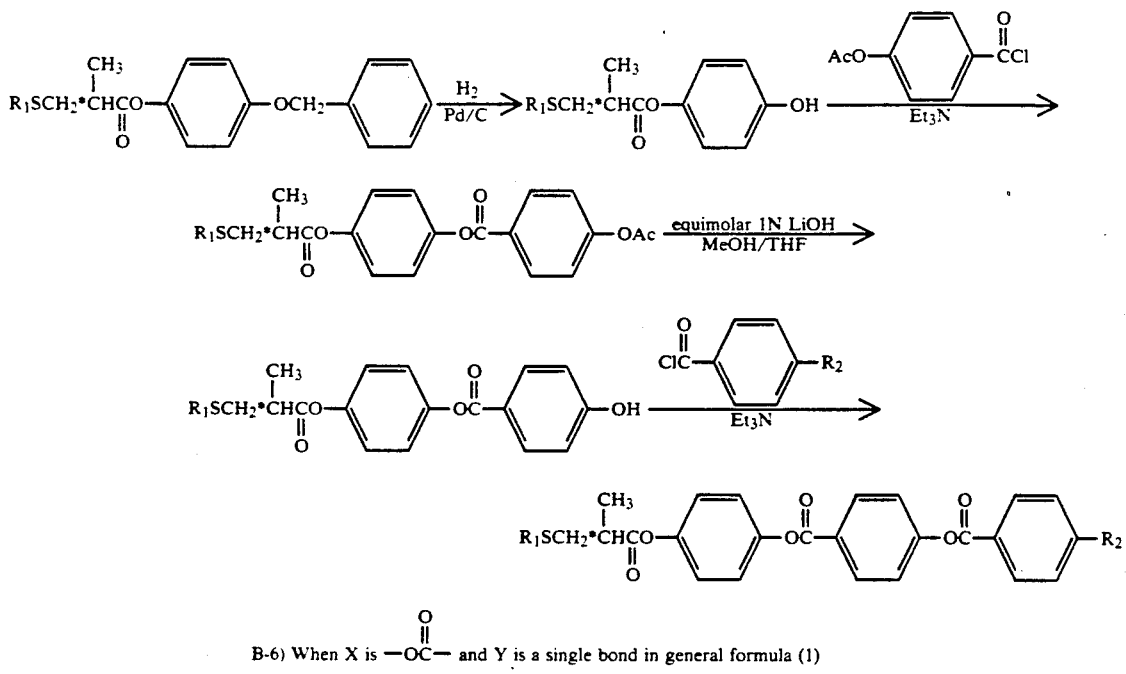
B-6) When X is —OC(=O)— and Y is a single bond in general formula (1)
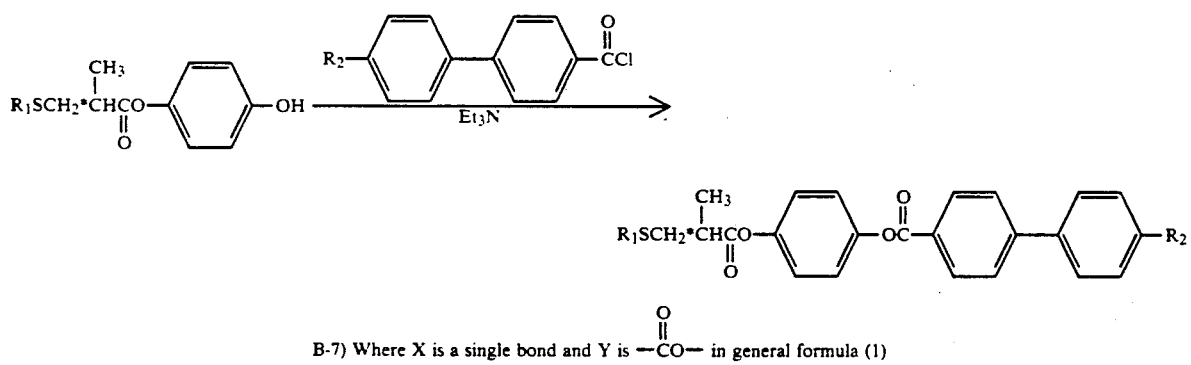
B-7) Where X is a single bond and Y is —C(=O)O— in general formula (1)
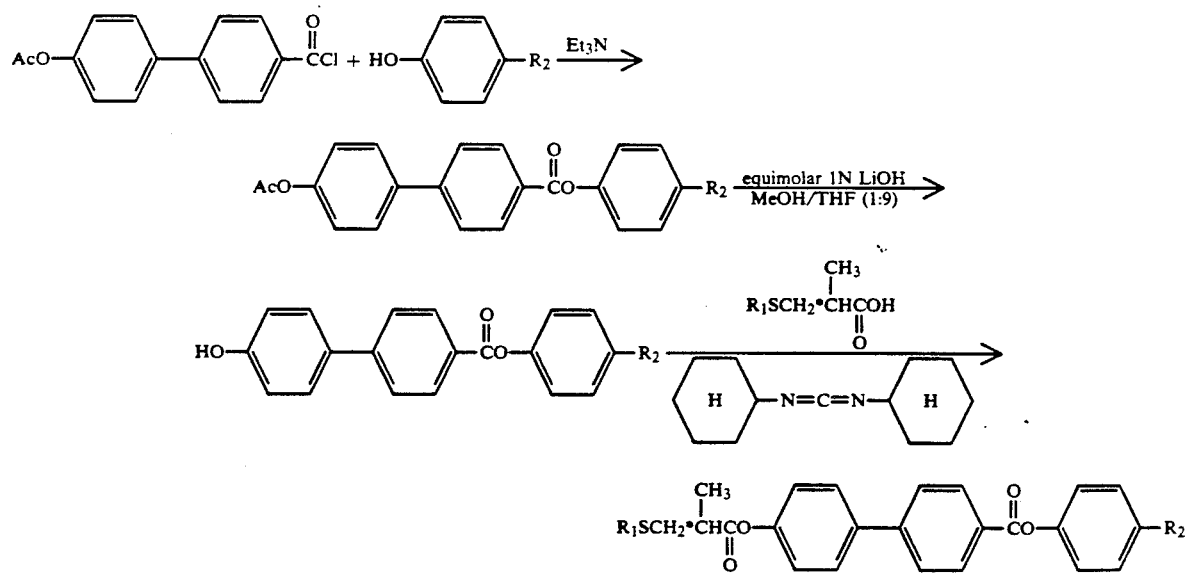
B-8) Where X is a single bond and Y is —OC(=O)— in general formula (1)

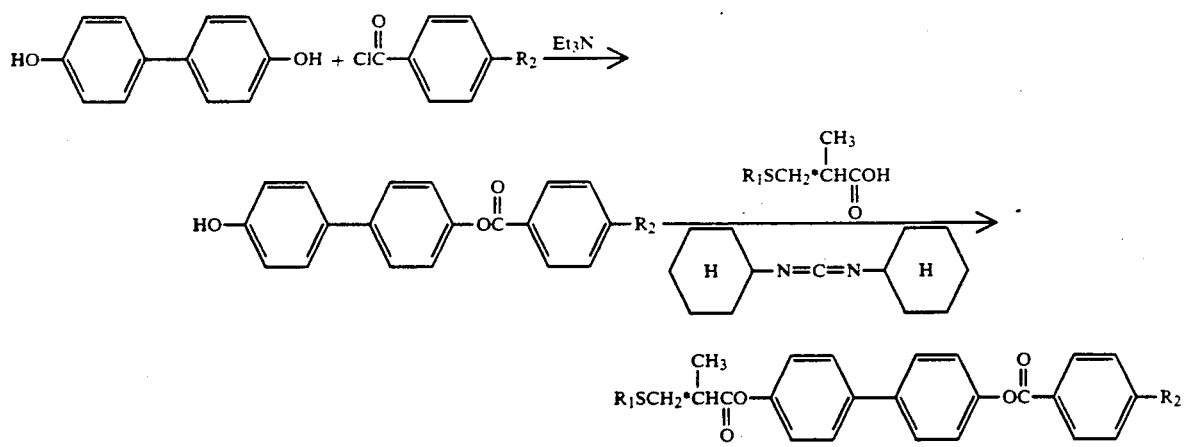

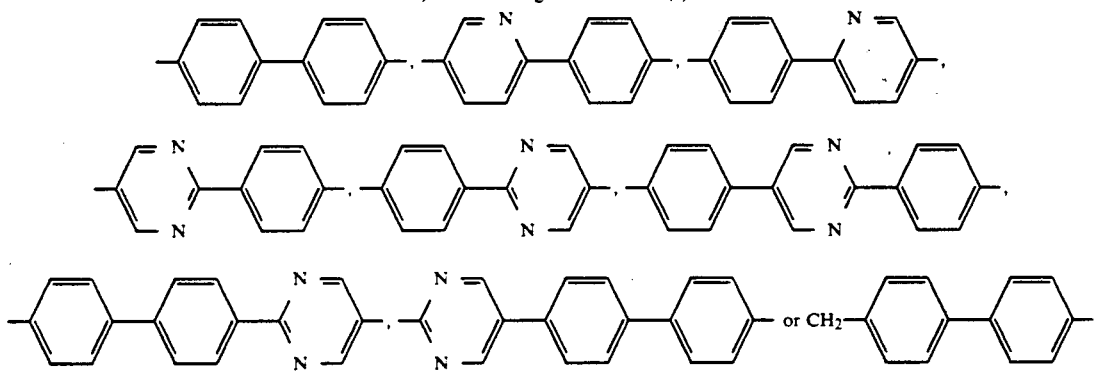

B-9) Where A in general formula (1) is

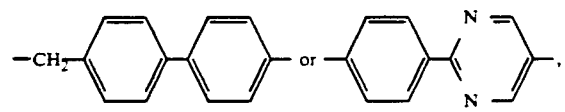

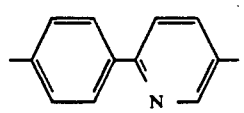

A synthetic product or commercially available product of corresponding HO-A-R$_2$ is esterified with an optically active 3-alkylthio-2-methylpropionic acid by using dicyclohexyl-carbodiimide as the dehydrating agent.

A commercially available product can be used for HO-A-R$_1$ in which A is

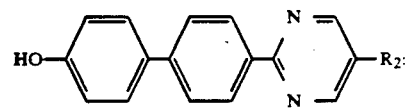

and HO-A-R$_2$ in which A is

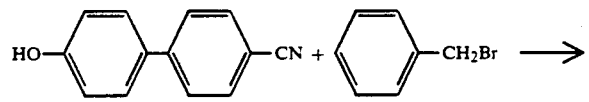

can be synthesized by the process disclosed in Japanese Unexamined Patent Publication No. 62-148469. Furthermore, HO-A-R$_2$ in which A is

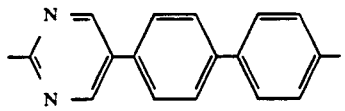

can be synthesized by the process disclosed in DT 2641724, and HO-A-R$_2$ in which A is

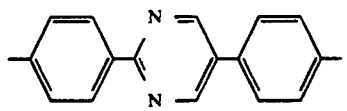

can be synthesized by the process disclosed in Japanese Unexamined Patent Publication No. 63-170367.

Furthermore, the following compounds can be synthesized through the routes described below.

-continued

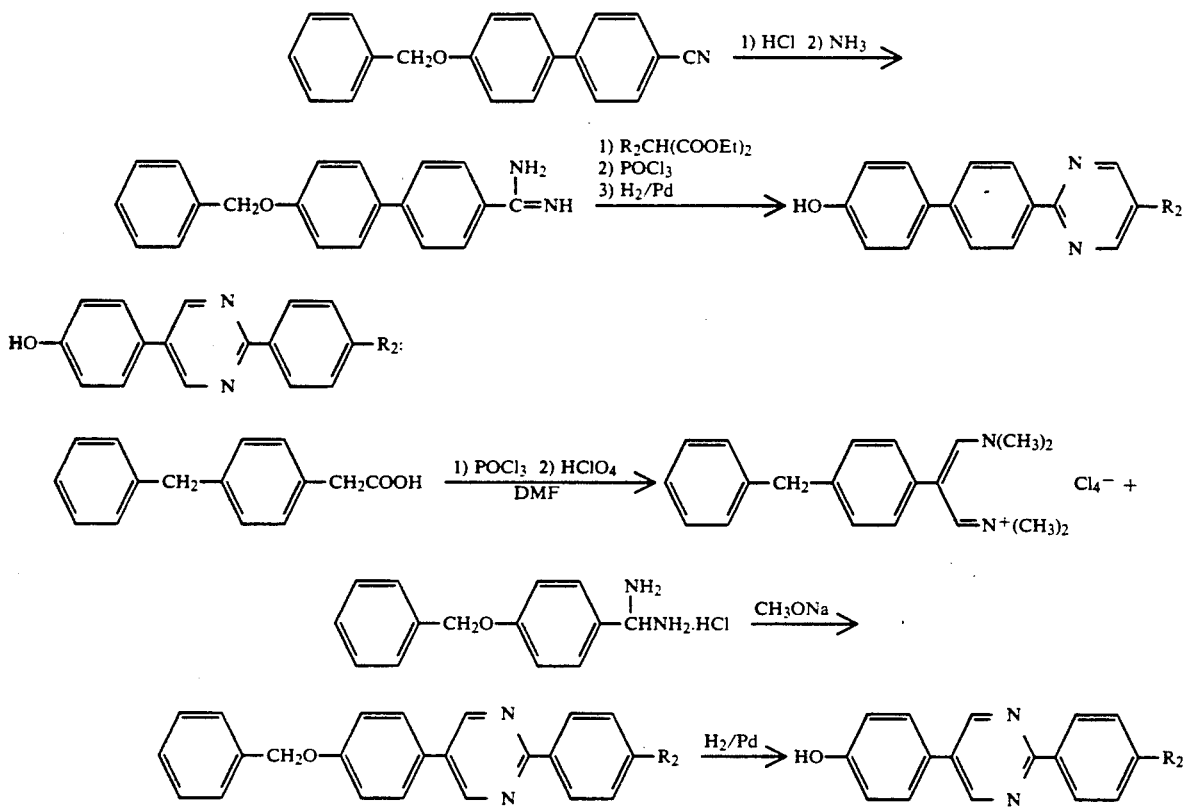

Some optically active compounds of the present invention show a liquid crystal phase per se, and other optically active compounds of the present invention do not show a liquid crystal phase. The former compounds are valuable as a constituent of a liquid crystal composition, and since the latter compounds induce a ferroelectric phase (Sm*C phase) if ethyl are incorporated in amounts of 1 to 90 mol% into non-chiral liquid crystals having a phase system of isotropic phase-nematic phase (N phase)-smectic A phase (SmA phase)-smectic C phase (SmC phase) or isotropic-N phase-SmC phase or mixtures thereof within a range not destroying the liquid crystal property, these compounds are preferably used as additives when ferroelectric liquid crystal compositions are prepared.

In a display element comprising a ferroelectric liquid crystal it is considered that, for the ferroelectric liquid crystal to take a good orientation state, preferably the cholesteric phase (Ch phase) is present on the higher temperature side than the Sm*C phase. The optically active compound of the present invention is characterized in that many compounds having the cholesteric phase on the higher temperature side than the Sm*C phase are included.

The compound of the present invention has a spontaneous polarization as large as scores of nC/cm², and when the compound of the present invention is mixed with other ferroelectric liquid crystal compound, the compound of the present invention exerts an excellent effect of increasing the spontaneous polarization and expanding the temperature range showing the ferroelectric property without lowering the ferroelectric property.

Moreover, since the structure of the compound of the present invention does not contain an azomethine bond, which is observed in most conventional ferroelectric compounds, the compound of the present invention has an excellent chemical stability, for example, resistance to the hydrolysis, and is not colored. Furthermore, since the structure of the compound of the present invention does not contain a vinyl group, which is observed in cinnamic acid type compounds, the compound of the present invention has an excellent light stability.

The liquid crystal composition of the present invention will now be described.

The liquid crystal composition of the present invention comprises at least one member selected from the group consisting of compounds represented by the general formula (1), but if a liquid crystal composition is formed by using a plurality of ferroelectric compounds of the formula (1), optionally with other additive compounds, the usable temperature range can expanded, compared with a composition formed by using one compound of the formula (1). Moreover, since the compound of the present invention includes a compound having a large tilt angle and a compound having a smaller tilt angle, a desired tilt angle can be easily obtained by mixing these compounds at an appropriate mixing ratio, and a composition suitable for a birefringence type display element or guest-host type display element can be prepared. The present invention is advantageous also in this point. As specific examples of other ferroelectric liquid crystal compounds that can be mixed with at least one compound represented by the general formula (1), the following compounds can be mentioned:

$C_nH_{2n+1}O-X-\overset{O}{\underset{\|}{C}}O-Y-O^*R$ (n = 7-12, X =

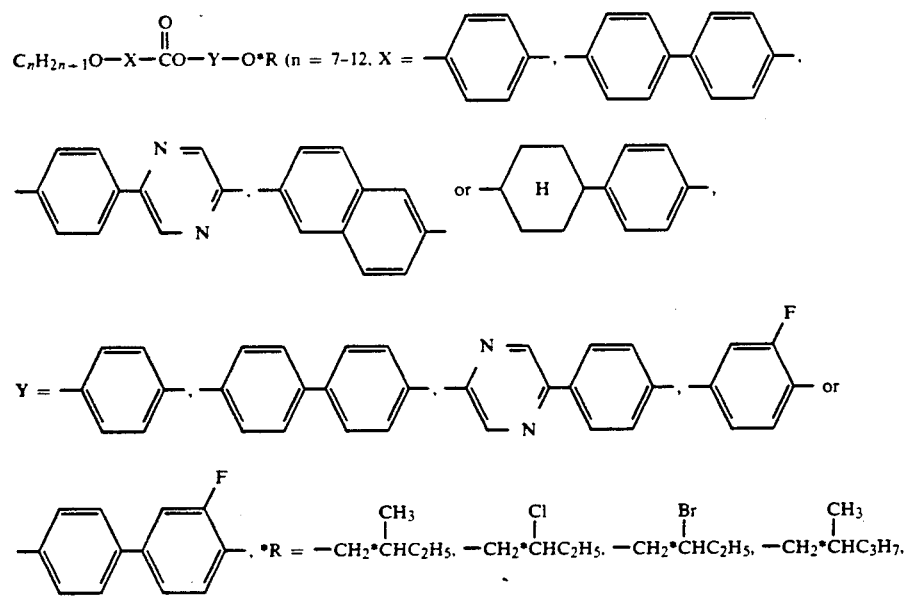

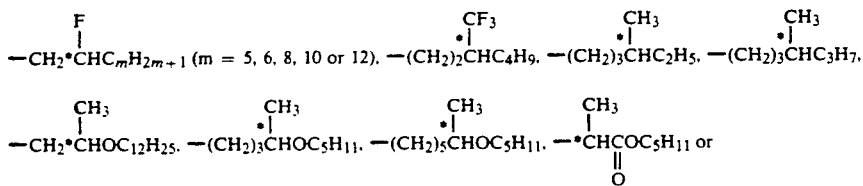

$-CH_2{}^*\overset{F}{\underset{|}{C}}HC_mH_{2m+1}$ (m = 5, 6, 8, 10 or 12), $-(CH_2)_2{}^*\overset{CF_3}{\underset{|}{C}}HC_4H_9$, $-(CH_2)_3{}^*\overset{CH_3}{\underset{|}{C}}HC_2H_5$, $-(CH_2)_3{}^*\overset{CH_3}{\underset{|}{C}}HC_3H_7$, $-CH_2{}^*\overset{CH_3}{\underset{|}{C}}HOC_{12}H_{25}$, $-(CH_2)_3{}^*\overset{CH_3}{\underset{|}{C}}HOC_5H_{11}$, $-(CH_2)_5{}^*\overset{CH_3}{\underset{|}{C}}HOC_5H_{11}$, $-{}^*\overset{CH_3}{\underset{|}{C}}H\overset{O}{\underset{\|}{C}}OC_5H_{11}$ or

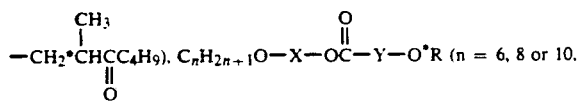

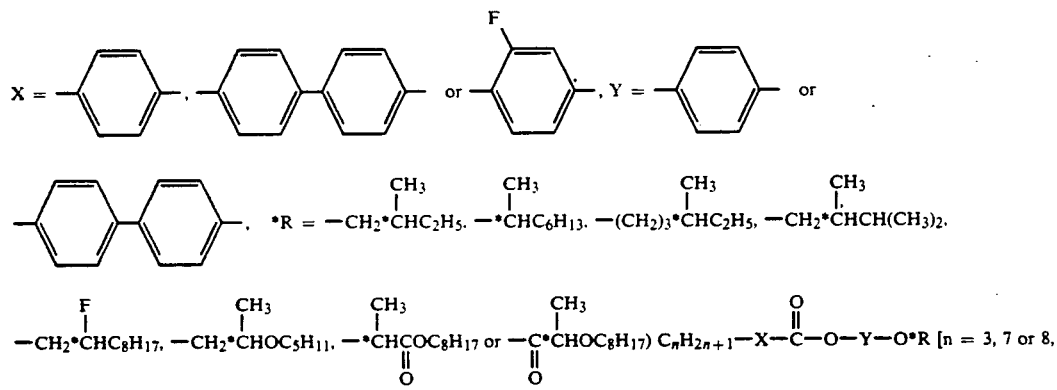

$-CH_2{}^*\overset{F}{\underset{|}{C}}HC_8H_{17}$, $-CH_2{}^*\overset{CH_3}{\underset{|}{C}}HOC_5H_{11}$, $-{}^*\overset{CH_3}{\underset{|}{C}}H\overset{O}{\underset{\|}{C}}OC_8H_{17}$ or $-\overset{O}{\underset{\|}{C}}{}^*\overset{CH_3}{\underset{|}{C}}HOC_8H_{17}$) $C_nH_{2n+1}-X-\overset{O}{\underset{\|}{C}}-O-Y-O^*R$ [n = 3, 7 or 8,

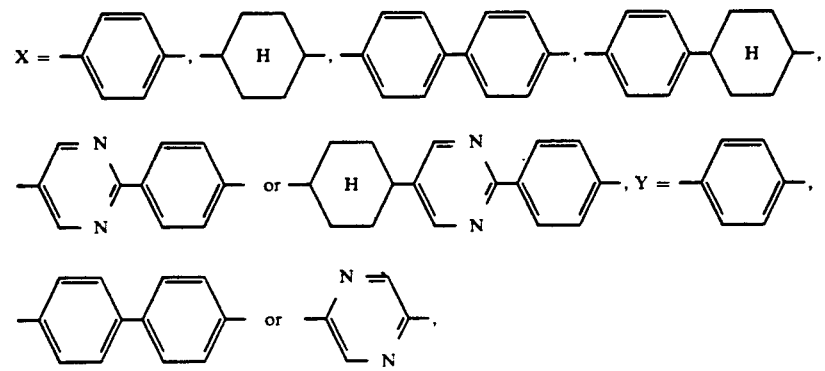

-continued

*R = —CH$_2$*CHC$_m$H$_{2m+1}$ (m = 2 or 6) or —CH$_2$*CHC$_m$H$_{2m+1}$ (m = 5, 6 or 8, Z = F or Cl)].

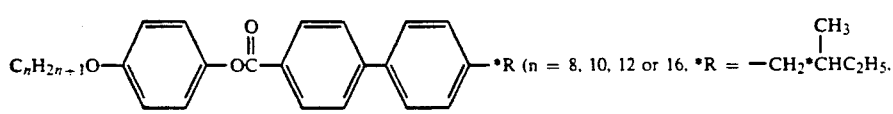 (n = 8, 10, 12 or 16, *R = —CH$_2$*CHC$_2$H$_5$,

—OCH$_2$*CHC$_2$H$_5$, —OCH$_2$*CHC$_3$H$_7$, —OCH$_2$*CHC$_8$H$_{17}$,

—OCH$_2$*CHOC$_4$H$_9$ or —OCH$_2$*CHOC$_8$H$_{17}$), 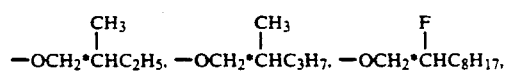

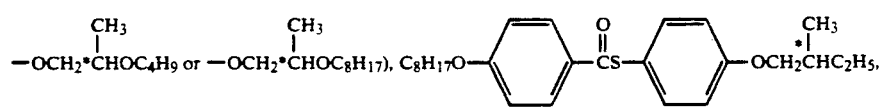

*R = —CH$_2$*CHOC$_5$H$_{11}$ or —CH$_2$*CHC$_6$H$_{13}$), C$_n$H$_{2n+1}$O—X—CO—Y—CO*R (n = 5–8, 10 or 12, X and Y = 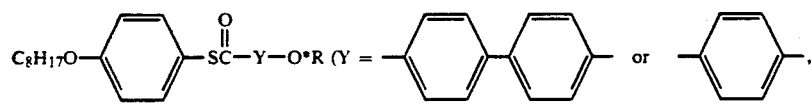

with the proviso that at least one of X and Y is 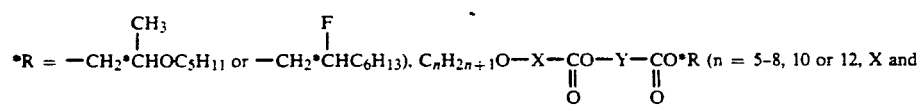, *R = —CH$_2$*CHC$_2$H$_5$, —CH$_2$*CHC$_6$H$_{13}$, —*CHC$_8$H$_{17}$, —CH$_2$*CHOC$_5$H$_{11}$, —(CH$_2$)$_5$*CHOC$_5$H$_{11}$, —*CHC$_6$H$_{13}$, —*CHOC$_2$H$_5$ or —*CHCH$_2$COC$_2$H$_5$), C$_n$H$_{2n+1}$O—X—CO*R (n = 5, 7, 8 or 12, X = 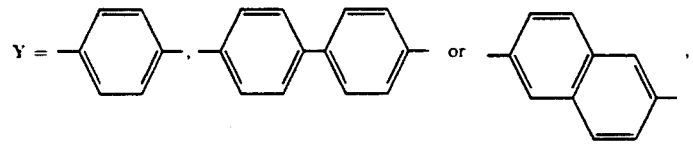

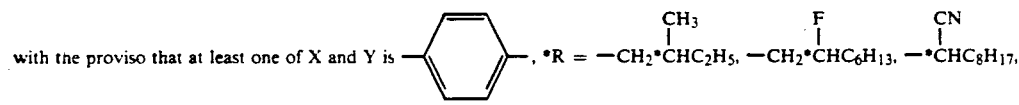

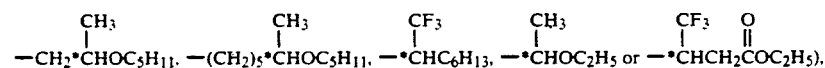, *R = —(CH$_2$)$_3$*CHC$_2$H$_5$, —CH$_2$*CHC$_6$H$_{13}$, —CH$_2$*CHC$_8$H$_{17}$ or —*CHC$_8$H$_{17}$), R'—X—O*R (R' = —C$_8$H$_{17}$, —C$_9$H$_{19}$, —C$_{10}$H$_{21}$, —OC$_{10}$H$_{21}$ or —C$_{11}$H$_{23}$, X = 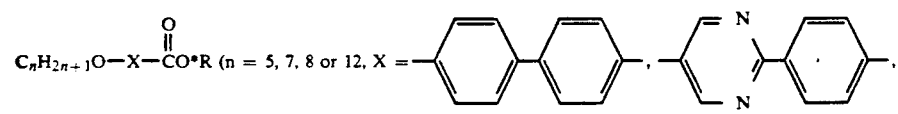 or

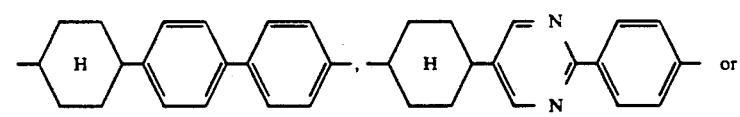, *R = —(CH$_2$)$_5$*CHC$_2$H$_5$, —(CH$_2$)$_3$*CHC$_2$H$_5$, —(CH$_2$)$_2$*CHC$_2$H$_5$, —(CH$_2$)$_3$*CHOC$_5$H$_{11}$, -continued
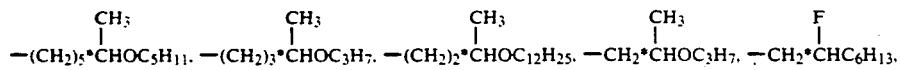
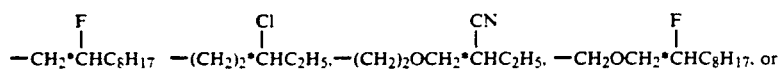
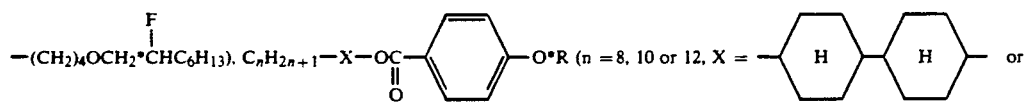
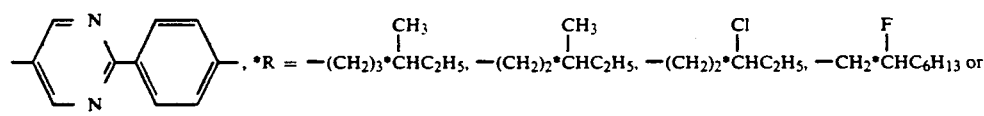
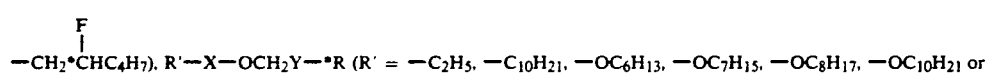
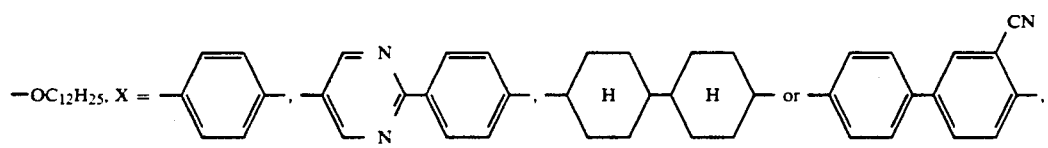
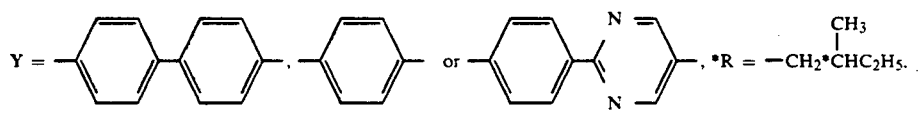
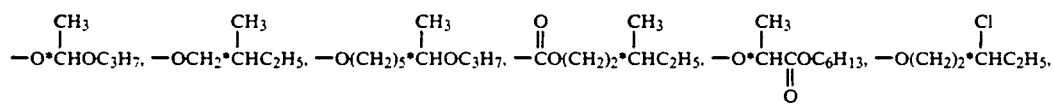
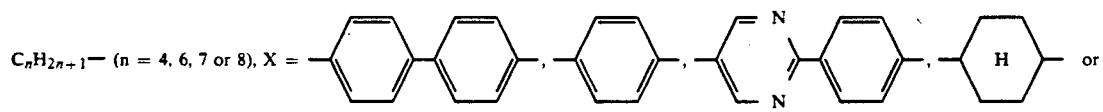
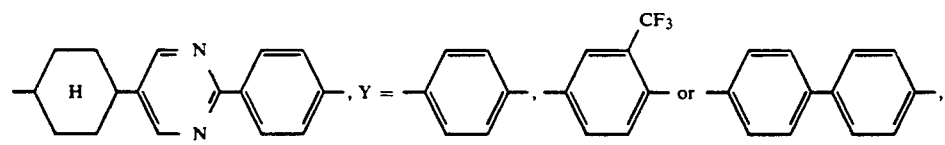
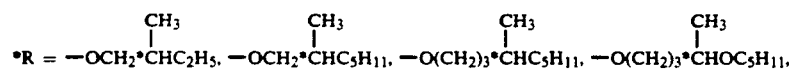
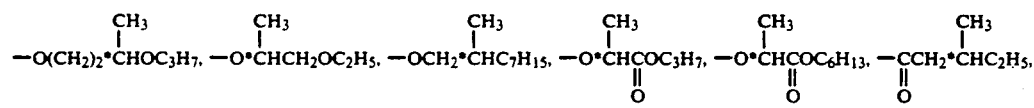
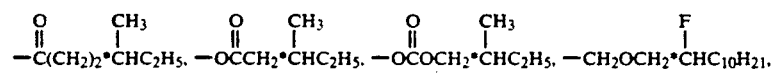
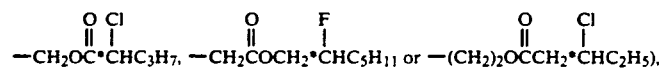

-continued
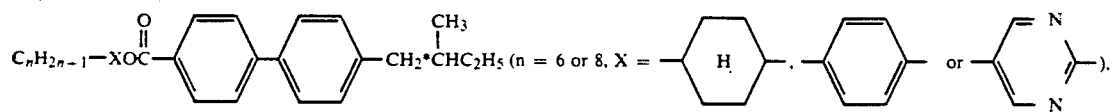
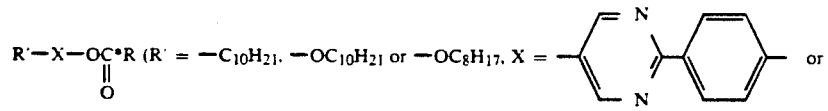
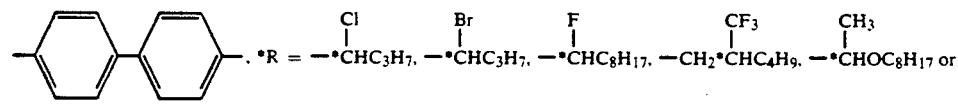
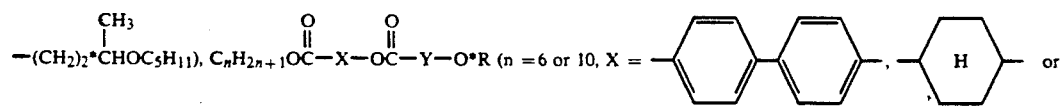
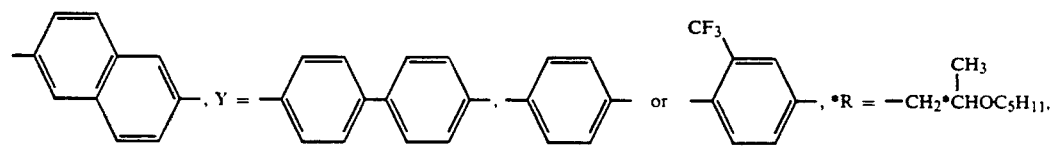
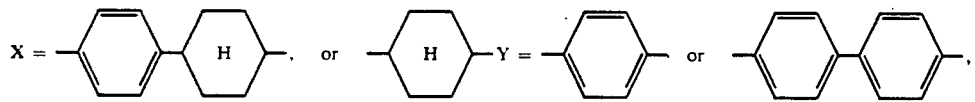
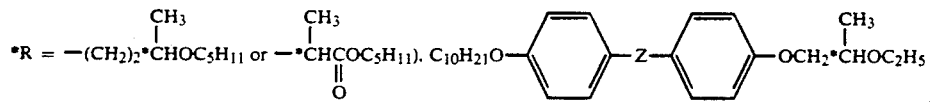
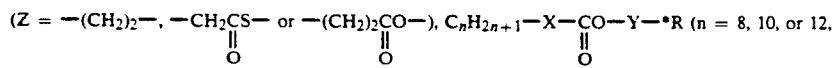
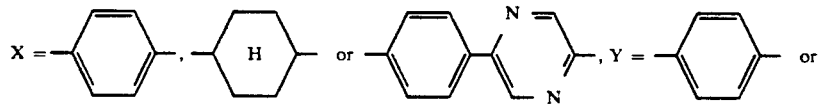
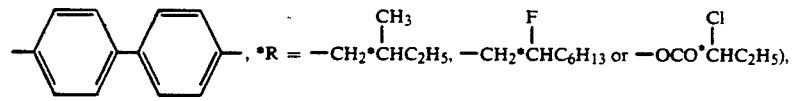
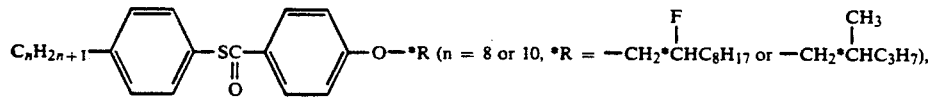
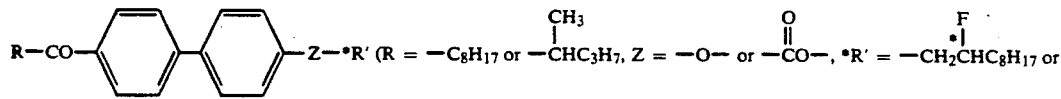
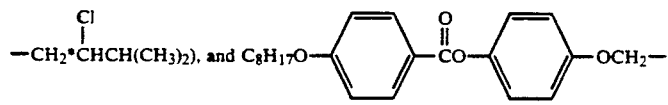

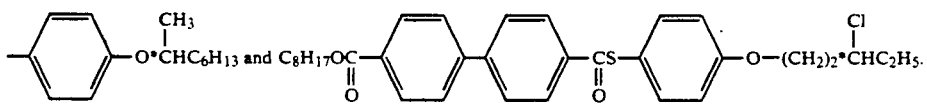

When the optically active compound of the present invention is mixed with a non-ferroelectric liquid crystal compound or composition exhibiting an SmC phase, the resulting mixture is a ferroelectric liquid crystal having a high response speed, i.e., exhibiting a large spontaneous polarization. The non-ferroelectric crystal compound that can be mixed with the compound of the present invention, there can be mentioned compounds represented by the following formula:

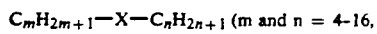

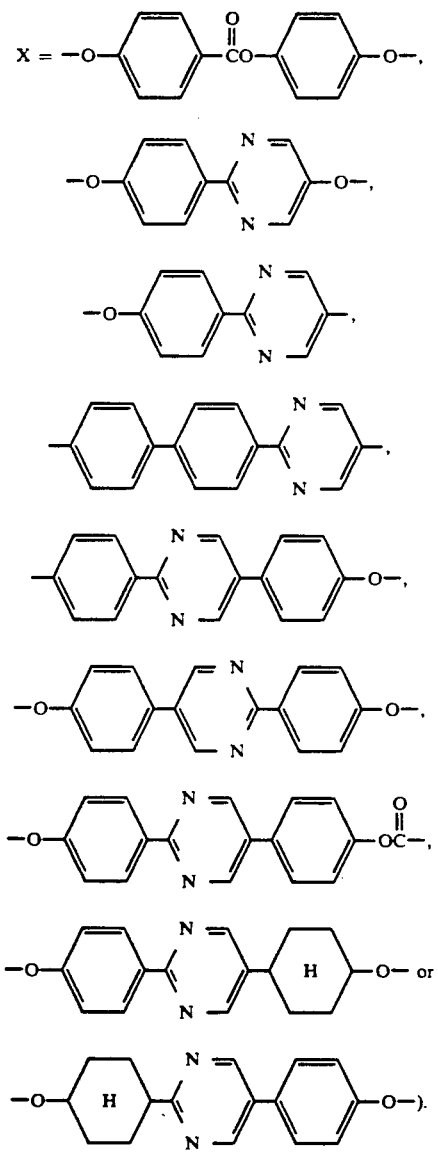

Ferroelectric liquid crystal compounds other than the above-mentioned compounds can be used in the form of mixtures with compounds of the general formula (1).

The present invention will now be described in detail with reference to the following examples.

Referential Example 1

Synthesis of 3-alkylthio-2-methylpropionic acid (the case wherein the alkyl group is a butyl group is described as a typical instance)

In 150 ml of water was dissolved 60 g of sodium hydroxide, 150 ml of ethanol was added to the solution, and 66.5 g (0.5 mol) of methyl L-(+)-β-acethylthio-α-methylpropionate was added to the mixture. The mixture was stirred at room temperature for 1 hour, 109.6 g (0.8 mol) of n-butyl bromide was added to the mixture, and a reaction was carried out at room temperature overnight. Then 1N hydrochloric acid was added to the reacted mixture to effect neutralize, the reacted mixture was extracted with diethyl ether, the extract was washed three times with dilute hydrochloric acid and water in this order and dried with anhydrous magnesium sulfate, and the solvent was evaporated to obtain 56.2 g of optically active 3-butylthio-2-methylpropionic acid.

The obtained optically active 3-butylthio-2-methylpropionic acid was preserved on a molecular sieve.

Referential Example 2

Synthesis of

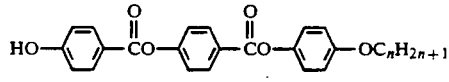

(the case wherein n is 8 is described as a typical instance)

In diethyl ether was dissolved 1.83 g ($8.24 \times 10^{-3}$ mol) of 4-n-octyloxyphenol, 1.65 g ($8.24 \times 10^{-3}$ mol) of 4-acetoxybenzoic acid chloride was incorporated and dissolved in the solution, and 1.67 g ($1.65 \times 10^{-2}$ mol) of triethylamine was then added to the solution and a reaction was carried out at room temperature, with stirring, overnight. Then the reacted solution was washed three times with 1N hydrochloric acid, a 1N aqueous solution of sodium hydrogencarbonate, and water, in this order, the ether solution was dried with anhydrous magnesium sulfate, and diethyl ether was evaporated to obtain 2.23 g of (4-n-octyloxy)phenyl 4-acetoxybenzoate. This product was dissolved in 100 ml of a THF/methanol (9/1) mixed solvent and 5.81 ml ($5.81 \times 10^{-3}$ mol) of a 1N aqueous solution of lithium hydroxide was added to the solution cooled with ice-cold water, and reaction was carried out with stirring for 30 minutes. Then the reacted solution was made weakly acidic by addition of 1N hydrochloric acid and extracted with diethyl ether, and the extract was washed three times with 1N hydrochloric acid, a 1N aqueous solution of sodium hydrogencarbonate, and water, in this order. The organic phase was recovered and dried with anhydrous magnesium sulfate, and the organic solvent was evaporated to obtain 1.79 g of 4-n-octyloxyphenyl 4-hydroxybenzoate.

The product was dissolved in 150 ml of diethyl ether and 1.04 g (5.23×10⁻³ mol) of 4-acetoxybenzoic acid chloride was added into the solution, and 1.06 g (1.46×10⁻² mol) of triethylamine was added to the solution and a reaction was carried out at room temperature with stirring overnight. Then the reacted mixture was washed three times with 1N hydrochloric acid, a 1N aqueous solution of sodium hydrogencarbonate, and water in this order, the ether solution was dried with anhydrous magnesium sulfate, and diethyl ether was evaporated. The product was isolated from the residue by a silica gel column chromatography using benzene/n-hexane mixed solvent as eluant and 1.84 g of 4-n-octyloxyphenyl 4-(4-acetoxy-benzoyloxy)benzoate was obtained.

The product was dissolved in a THF/methanol (9/1) mixed solvent, and 3.65 ml (3.65×10⁻³ mol) of a 1N aqueous solution of lithium hydroxide was added to the solution cooled with ice-cold water and a reaction was carried out for 30 minutes with stirring. Then the reacted mixture was made weakly acidic by an addition of 1N hydrochloric acid and extracted with a diethyl ether/benzene (1/1) mixed solvent The extract was washed three times with 1N hydrochloric acid, a 1N aqueous solution of sodium hydrogencarbonate and water, in this order, the organic layer was recovered and dried with anhydrous magnesium sulfate, and the organic solvent was evaporated to obtain 1.52 g of 4-n-octyloxyphenyl 4-(4-hydroxybenzoyloxy)benzoate. The product was recrystallized from an n-hexane/ethanol mixed solvent to obtain 0.597 g of a purified product.

Referential Example 3

Synthesis of

(the case wherein n is 7 is described as a typical instance)

In diethyl ether was dissolved 2.84 g (0.01 mol) of 4-n-heptyloxybiphenol, and 1.99 g (0.01 mol) of 4-acetoxybenzoic acid chloride was added into the solution. Then 2.02 g of (0.02 mol) of triethylamine was added to the solution and a reaction was carried out at room temperature with stirring overnight. The reacted mixture was washed three times with 1N hydrochloric acid, a 1N aqueous solution of sodium hydrogencarbonate, and water, in this order, the ether solution was dried with anhydrous magnesium sulfate, diethyl ether was evaporated, and the reaction product was isolated from the residue by silica gel chromatography using benzene/n-hexane as eluant and 3.12 g of 4'-n-heptyloxybiphenyl 4-(4-acetoxybenzoate) was obtained.

The product was dissolved in 100 ml of a THF/methanol (9/1) mixed solvent, and 7 ml of a 1N aqueous solution of lithium hydroxide was added to the solution cooled with ice-cold water and reaction was carried out for 30 minutes with stirring. Then the reacted mixture was made weakly acidic by an addition of 1N hydrochloric acid and extracted with a diethyl ether/benzene (1/1) mixed solvent. The extract was washed three times with 1N hydrochloric acid, a 1N aqueous solution of sodium hydrogencarbonate, and water, in this order. The organic phase was recovered and dried with anhydrous magnesium sulfate, and the organic solvent was evaporated to obtain 2.52 g of 4'-n-heptyloxybiphenyl 4-(4-hydroxybenzoate.) The product was recrystallized from an n-hexane/ethanol mixed solvent to obtain 1.83 g of a purified product.

Referential Example 4

Synthesis of

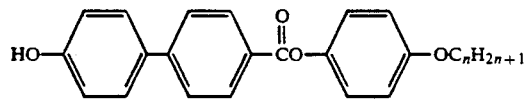

(the case wherein n is 7 is described as a typical instance)

In 150 ml of pyridine was dissolved 12.5 g (0.0584 mol) of 4,4'-hydroxybiphenylcarboxylic acid, and 10 g of acetic anhydride was added to the solution and reaction was carried out at room temperature with stirring overnight. The reacted solution was dropped into a 0.5N aqueous solution of hydrochloric acid to precipitate the reaction product, and the reaction product was recovered by filtration to obtain white powder. The white powder was vacuum-dried and recrystallized from an acetic acid/pyridine (2/1) mixed solvent to obtain 9.3 g of 4,4'-acetoxybiphenylcarboxylic acid. To 2.56 g of the so-obtained 4,4'-acetoxybiphenylcarboxylic acid was added 15 g of thionyl chloride, and reaction was carried out under reflux for 3 hours. The unreacted thionyl chloride was removed by distillation under a reduced pressure to obtain 4,4'-acetoxybiphenylcarboxylic acid chloride quantitatively. Then 2.74 g of 4,4'-acetoxybiphenylcarboxylic acid chloride was dissolved in 200 ml of THF, 1.80 g of 4-n-heptyloxyphenol and 2 g of triethylamine were added to the solution successively, and the mixture was reacted at room temperature with stirring overnight. The product was extracted from the reacted mixture with 200 ml of benzene, and the extract was washed three times with 1N hydrochloric acid, a 1N aqueous solution of sodium hydrogencarbonate and water, in this order. The organic phase was recovered and dried with anhydrous magnesium sulfate, the organic solvent was evaporated, and the reaction product was isolated from the residue by silica gel column chromatography using a benzene/n-hexane mixed solvent as eluant, whereby 2.60 g of 4-n-heptyloxyphenyl 4,4'-acetoxybiphenylcarboxylate was obtained.

The product was dissolved in 100 ml of a THF/methanol (9/1) mixed solvent, 6.2 ml of a 1N aqueous solution of lithium hydroxide was added to the solution cooled with ice-cold water, and reaction was carried out with stirring for 30 minutes. Then the reacted solution was made weakly acidic by an addition of 1N hydrochloric acid and extracted with a diethyl ether/benzene (1/1) mixed solvent. The extract was washed three times with 1N hydrochloric acid, a 1N aqueous solution of sodium hydrogencarbonate and water, in this order. The organic phase was recovered and dried with anhydrous magnesium sulfate, and the organic solvent was evaporated to obtain 4-n-heptyloxyphenyl 4,4'-hydroxybiphenylcarboxylate. The product was recrystallized from an n-hexane/ethanol mixed solvent to obtain 1.53 g of a purified product.

Referential Example 5

Synthesis of

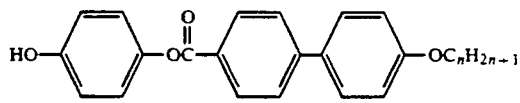

(the case wherein n is 10 is described as a typical instance)

To 1.46 g of 4,4'-decyloxybiphenylcarboxylic acid was added 15 g of thionyl chloride, a reaction was carried out under reflux for 3 hours, and the unreacted chloride was removed by distillation under a reduced pressure to obtain 4,4'-n-decyloxybiphenylcarboxylic acid chloride quantitatively. Then the product was dissolved in a diethyl ether/THF (1/1) mixed solvent, 0.83 g of 4-benzyloxyphenol and 1.6 g of triethylamine were added to the solution successively, and the mixture was stirred at room temperature overnight to effect a reaction.

Since the reaction product was obtained in the form of a precipitate, washing and filtration were carried out with 1N hydrochloric acid, 1N sodium hydrogencarbonate and water, in this order, to obtain 1.68 g of a white precipitate. THF was added to the precipitate, and the precipitate was dissolved in hot THF. Then 3 g of 5%Pd/C was added to the solution and reaction was carried out at room temperature in a hydrogen atmosphere overnight. The Pd/C was removed by filtration, the solvent was removed from the reacted solution, and the residue was recrystallized from an n-hexane/ethanol mixed solvent to obtain 0.83 g of a product.

Referential Example 6

Synthesis of

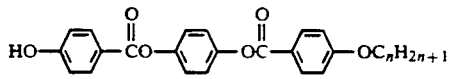

(the case wherein n is 10 is described as a typical instance)

In diethyl ether were dissolved 1.99 g of 4-acetoxybenzoic acid chloride and 2.00 g of 4-benzyloxyphenol, 2.00 g of triethylamine was added to the solution, and a reaction was carried out at room temperature with stirring overnight. The reacted mixture was washed three times with 1N hydrochloric acid, a 1N aqueous solution of sodium hydrogencarbonate and water, in this order, and the ether solution was dried with anhydrous magnesium sulfate. Diethyl ether was evaporated and the product was isolated from the residue by silica gel column chromatography using benzene/n-hexane mixed solvent as eluant and 2.81 g of 4-benzyloxyphenyl 4-acetoxybenzoate was obtained. Then ethyl acetate was added to the reaction product to dissolve the reaction product, 6 g of 5%Pd/C was added to the solution, and a reaction was carried out at room temperature in a hydrogen atmosphere overnight. The Pd/C was removed by filtration, the solvent was removed from the reacted solution, and the residue was recrystallized from an n-hexane/ethanol mixed solvent to obtain 2.24 g of 4-acetoxybenzoyloxy-4-phenol. The product was dissolved in 100 ml of diethyl ether, 2.08 g of 4-n-decyloxybenzoic acid chloride and 1.40 g of triethylamine were added to the solution successively, and a reaction was carried out with stirring at room temperature overnight. The product was extracted from the reacted solution with 200 ml of benzene, and the extract was washed three times with 1N hydrochloric acid, a 1N aqueous solution of sodium hydrogencarbonate and water, in this order. The organic phase was recovered and dried with anhydrous magnesium sulfate, the organic solvent was evaporated, and the residue was dissolved in 100 ml of a THF-methanol (9/1) mixed solvent. Then 1 ml of a 1N aqueous solution of lithium hydroxide was added to the solution cooled with ice-cold water and a reaction was carried out with stirring for 30 minutes. The reacted mixture was made weakly acidic by an addition of 1N hydrochloric acid, extracted with a diethyl ether/benzene (1/1) mixed solvent, and the extract was washed three times with 1N hydrochloric acid, a 1N aqueous solution of sodium hydrogencarbonate and water, in this order. The organic phase was recovered and dried with anhydrous magnesium sulfate, the organic solvent was evaporated, and the product was isolated from the residue by silica gel column chromatography using benzene/n-hexane as eluant and 4-hydroxybenzoyloxyphenyl 4-decyloxybenzoate was obtained. The product was recrystallized from an n-hexane/ethanol mixed solvent to obtain 2.19 g of a purified product.

Referential Example 7

Synthesis of

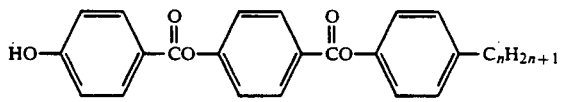

(the case wherein n is 7 is described as a typical instance)

4-n-Heptylphenyl 4-(4-hydroxybenzoyloxy)benzoate was synthesized in the same manner as described in Referential Example 2 except that 1.58 g (8.24×10⁻³ mol) of 4-n-butylphenol was used instead of 1.83 g (8.24×10⁻³ mol) of 4-n-octyloxyphenol. The product was recrystallized from an n-hexane/ethanol mixed solvent to obtain 0.86 g of a purified product.

Referential Example 8

Synthesis of

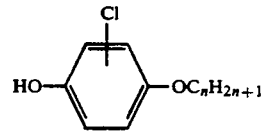

(the case wherein n is 8 is described as a typical instance)

In 100 ml of ethanol were dissolved 14.5 g of chlorohydroquinone and 19.3 g of n-octyl bromide, an aqueous solution of 6 g of sodium hydroxide in 100 ml of water was added to the above solution, and a reaction was carried out under reflux for 10 hours. The reacted mixture was neutralized with 1N hydrochloric acid, extracted with ether and washed with water, and the organic phase was recovered and dried. Then ether was removed under a reduced pressure, and 2 g of 2-chloro-4-octyloxyphenol and 6 g of 3-chloro-4-octyloxyphenol were recovered by silica gel column chromatography.

Alkoxyphenols in which n is other than 8 can be similarly obtained by using corresponding n-alkyl bromides instead of n-octyl bromide.

Referential Example 9

Synthesis of

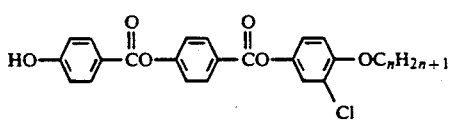

(the case wherein n is 8 is described as a typical instance)

In diethyl ether were dissolved 5.5 g of 3-chloro-4-octyloxyphenol obtained in Referential Example 8 and 4.3 g of 4-acetoxybenzoic acid chloride, 4 g of triethylamine was added to the solution, and a reaction was carried out at room temperature with stirring overnight. The reacted solution was washed three times with 1N hydrochloric acid, a 1N aqueous solution of sodium hydrogencarbonate and water, in this order, the enter solution was dried with anhydrous magnesium sulfate, and the solvent was evaporated. The reaction product recovered by silica gel column chromatography using benzene/n-hexane as eluant. Then the reaction product was dissolved in 100 ml of a THF/methanol (9/1) mixed solvent, a 1N aqueous solution of lithium hydroxide was added to the solution, and a reaction was carried out with stirring for 30 minutes. The reacted mixture was then made weakly acidic by an addition of hydrochloric acid and extracted with a diethyl ether/benzene (1/1) mixed solvent, and the extract was washed three times with 1N hydrochloric acid, a 1N aqueous solution of sodium hydrogencarbonate and water, in this order. The organic phase was recovered and dried with anhydrous magnesium sulfate, and the organic solvent was evaporated to obtain 4.2 g of a product. The product and 2 g of 4-acetoxybenzoic acid chloride were dissolved in a diethyl ether/THF mixed solvent, 2 g of triethylamine was added to the solution, and a reaction was carried out at room temperature with stirring overnight. The reacted mixture was washed three times with 1N hydrochloric acid, a 1N aqueous solution of sodium hydrogencarbonate and water, in this order, the ether solution was dried with anhydrous magnesium sulfate, and diethyl ether was evaporated. The reaction product was isolated from the residue by a silica gel column chromatography using a benzene/n-hexane mixed solvent as eluant. The reaction product was dissolved in 100 ml of a THF/methanol (9/1) mixed solvent, a 1N aqueous solution of lithium hydroxide was added to the solution cooled with ice-cold water, and a reaction was carried out with stirring for 30 minutes. Then, the reacted mixture was made weakly acidic by an addition of 1N hydrochloric acid and extracted with a diethyl ether/benzene (1/1) mixed solvent, and the extract was washed three times with 1N hydrochloric acid, a 1N aqueous solution of sodium hydrogencarbonate and water, in this order.

The organic phase was recovered and dried with anhydrous magnesium sulfate, and the organic solvent was evaporated to obtain 4.2 g of a product. The product was recrystallized from a hexane/ethanol mixed solvent.

Compounds in which n is other than 8 can be similarly prepared by using corresponding chloroalkoxyphenols.

Referential Example 10

Synthesis of

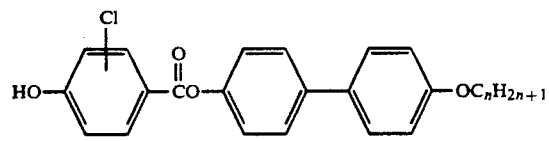

(the case wherein n is 10 is described as a typical instance)

To 3.5 g of 4,4'-decyloxybiphenylcarboxylic acid was added 15 g of thionyl chloride, and a reaction was carried out under reflux for 3 hours. The unreacted thionyl chloride was removed by distillation under a reduced pressure to quantitatively obtain 4,4'-n-decyloxybiphenylcarboxylic acid chloride. Then the reaction product was dissolved in a diethyl ether/THF (1/1) mixed solvent, 1.5 g of chlorohydroquinone and 2 g of trimethylamine were added to the solution successively, and a reaction was carried out at room temperature with stirring overnight. The reacted solution was the washed three times with 1N hydrochloric acid, a 1N aqueous solution of sodium hydrogencarbonate and water, in this order. The organic solution was dried with anhydrous magnesium sulfate, the organic solvent was removed by distillation under a reduced pressure, and 2-chloro-substituted and 3-chloro-substituted compounds were recovered by the silica gel column chromatography. The product was recrystallized from a benzene/hexane mixed solvent.

Compounds in which n is other than 10 can be similarly obtained by using 4,4'-n-alkoxybiphenylcarboxylic acids having a corresponding carbon number instead of 4,4'-decyloxybiphenylcarboxylic acid.

Referential Example 11

Synthesis of

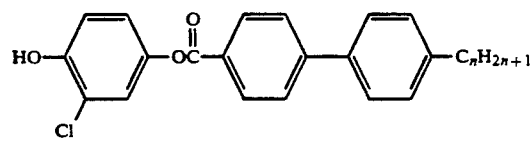

(the case wherein n is 10 is described as a typical instance)

The intended compound was prepared by repeating the procedures of Referential Example 10 in the same manner, except that 4,4'-decylbiphenylcarboxylic acid was used instead of 4,4'-decyloxybiphenylcarboxylic acid.

Referential Example 12

Synthesis of

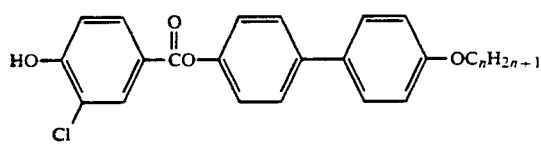

(the case wherein n is 10 is described as a typical instance)

In 200 ml of diethyl ether was dissolved 3.3 g of n-decyloxybiphenol, and 2.69 g of 3-chloro-4-acetoxybenzoic acid chloride was incorporated and dissolved in the solution. Then 2 g of triethylamine was added to the mixture and a reaction was carried out with stirring at room temperature overnight. The reacted mixture was then washed three times with 1N hydrochloric acid, a 1N aqueous solution of sodium hydrogensulfate and water, in this order, and the ether solution was dried with anhydrous magnesium sulfate and diethyl ether was evaporated. The product was isolated from the residue by silica gel column chromatography using benzene/n-hexane mixed solvent as eluant. Then the reaction product was dissolved in 100 ml of a THF/methanol (9/1) mixed solvent, a 1N aqueous solution of lithium hydroxide was added to the solution cooled with ice-cold water, and a reaction was carried out with stirring for 30 minutes. The reacted mixture was then made weakly acidic by addition of 1N hydrochloric acid and extracted with a diethyl ether/benzene (1/1) mixed solvent. The extract was washed three times with 1N hydrochloric acid, a 1N aqueous solution of sodium hydrogencarbonate and water, in this order, the organic phase was recovered and dried with anhydrous magnesium sulfate, and the organic solvent was evaporated to obtain a product. The product was recrystallized from an n-hexane/ethanol mixed solvent.

Referential Example 13

Synthesis of

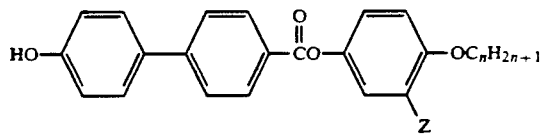

(the case wherein n is 10 and Z is chlorine is described as a typical instance)

In 100 ml of ethanol were dissolved 18 g of 1-bromo-n-decane and 9 g of 3-chloro-4-hydroxybenzoic acid, an aqueous solution of 40 g of sodium hydroxide in 100 ml of water was added to the above solution, and the mixture was heated and refluxed for 10 hours. Then the reacted solution was made weakly acidic by an addition of 1N hydrochloric acid and thrown in an enough quantity of water to precipitate the reaction product. The precipitate was recovered by filtration and recrystallized from ethanol to obtain 5 g of 3-chloro-4-decyloxybenzoic acid, then 15 g of thionyl chloride was added to 3 g of 3-chloro-4-decyloxybenzoic acid, and a reaction was carried out under reflux for 3 hours. The unreacted thionyl chloride was removed by distillation under a reduced pressure to obtain 3-chloro-4-decyloxybenzoic acid chloride quantitatively. Then the product was dissolved in a diethyl ether/THF (1/1) mixed solvent, 2.3 g of 4,4'-acetoxybiphenol and 2 g of triethylamine were added to the solution successively, and a reaction was carried out at room temperature with stirring overnight. The reacted solution was washed three times with 1N hydrochloric acid, a 1N aqueous solution of sodium hydrogencarbonate and water, in this order, and the organic phase was dried with anhydrous sodium sulfate. The solvent was evaporated, the reaction product was recovered by the silica gel chromatography, then the reaction product was dissolved in 100 ml of a THF/methanol (9/1) mixed solvent, a 1N aqueous solution of lithium hydroxide was added to the resulting solution which was cooled with ice-cold water, and a reaction was carried out with stirring for 30 minutes. Then the reacted solution was made weakly acidic by addition of 1N hydrochloric acid, extracted with a diethyl ether/benzene (1/1) mixed solvent, and the extract was washed three times with 1N hydrochloric acid, a 1N aqueous solution of sodium hydrogencarbonate and water in this order. The organic phase was recovered and dried with anhydrous magnesium sulfate, and the organic solvent was evaporated to obtain a product. The product was recrystallized from an n-hexane/ethanol mixed solvent. The compound in which Z is fluorine can be similarly obtained by using 3-fluoro-4-hydroxybenzoic acid instead of 3-chloro-4-hydroxybenzoic acid.

Referential Example 14

As the liquid crystal mixture having no optical activity, a mixture having the following composition was prepared:

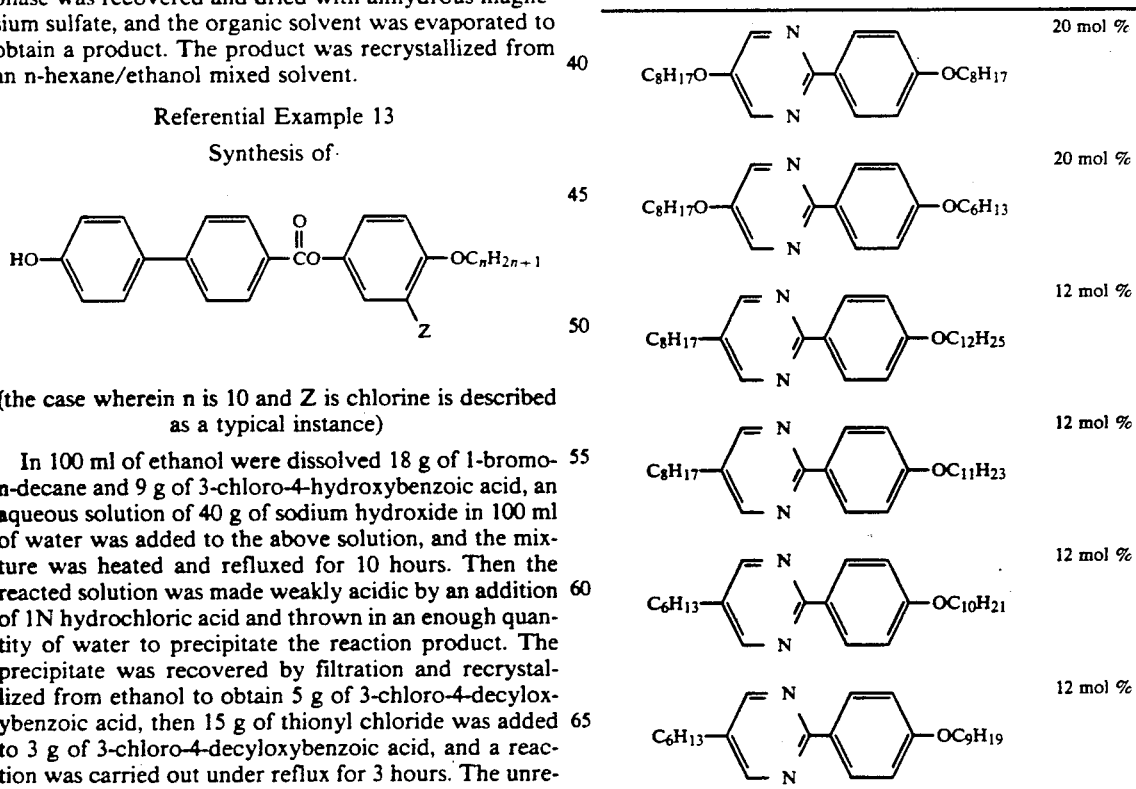

-continued

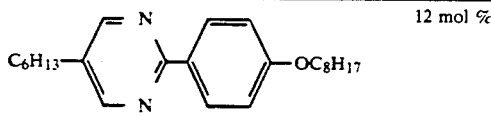
12 mol %

The phase transition temperatures (° C.) of the mixture were as follows:

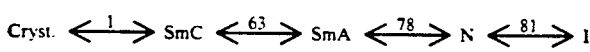

Cryst. ⇄¹ SmC ⇄⁶³ SmA ⇄⁷⁸ N ⇄⁸¹ Iso

EXAMPLE 1

Synthesis of

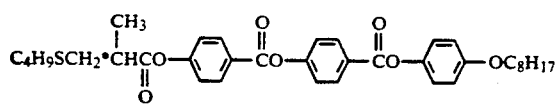

In 100 ml of methylene chloride were dissolved 1.76 g of optically active 3-butylthio-2-methylpropionic acid synthesized in Referential Example 1 and 4.9 g of 4-n-octyloxyphenyl 4-(4-hydroxybenzoyloxy)benzoate synthesized in the same manner as described in Referential Example 2, a solution of 2.26 g of dicyclohexylcarbodiimide in 10 ml of methylene chloride was dropped to the above solution, and a reaction was carried out at room temperature with stirring overnight. Then the reacted solution was washed three times with a 1N aqueous solution of sodium hydrogencarbonate and water, in this order, and the organic phase was recovered and dried with anhydrous magnesium sulfate. The organic solvent was evaporated the reaction product was isolated from the residue by silica gel chromatography using benzene/n-hexane as eluant and a white powder was obtained. The reaction product was recrystallized from an n-hexane/ethanol mixed solvent to obtain 4.12 g of a purified product. From the NMR spectrum and the elementary analysis, it was confirmed that the obtained compound was the intended product. The NMR spectrum of the obtained compound is shown in FIG. 1. The results of the elementary analysis were as shown below:

| | Carbon (%) | Hydrogen (%) | Sulfur (%) |
|---|---|---|---|
| Found values | 70.31 | 7.52 | 4.91 |
| Calculated values | 70.37 | 7.41 | 4.94 |

The phase transition temperatures and the value of spontaneous polarization (Ps) of compounds prepared according to the above-mentioned process are shown in Table 1.

TABLE 1

$$C_mH_{2m+1}SCH_2\text{*}CHCO\text{—}\phi\text{—}CO\text{—}\phi\text{—}CO\text{—}\phi\text{—}OC_nH_{2n+1}$$
(with CH₃ on chiral carbon, C=O)

| m | n | Phase Transition Temperatures (°C.) | Ps¹⁾ (nC/cm²) |
|---|---|---|---|
| 3 | 6 | Cryst ⇄⁷⁶·⁷ Sm*C ⇄⁷⁸·¹ Ch ⇄¹³⁰·⁶ Iso | 42 (−26° C.) |
| 3 | 7 | Cryst ⇄⁸⁸·⁶ Ch ⇄¹²³·⁷ Iso ; (58.9) Sm*C (84.9)²⁾ | 43 (−23° C.) |
| 3 | 8 | Cryst ⇄⁶²·⁶ Sm*C ⇄⁸⁰·³ Ch ⇄¹¹⁹·¹ Iso | 39 (−26° C.) |
| 3 | 10 | Cryst ⇄⁷²·⁶ Sm*C ⇄⁹²·⁷ Ch ⇄¹¹⁸·² Iso | 36 (−29° C.) |
| 4 | 8 | Cryst ⇄⁷²·⁶ Sm*C ⇄⁹³·⁶ Ch ⇄¹²¹·⁹ Iso | 44 (−36° C.) |
| 4 | 10 | Cryst ⇄⁷¹·⁷ Sm*C ⇄⁹⁴·⁹ Ch ⇄¹¹⁵·⁵ Iso | 37 (−32° C.) |
| 6 | 10 | Cryst ⇄⁶⁸·⁵ Sm*C ⇄¹⁰¹·⁸ Ch ⇄¹²⁵·¹ Iso | 20 (−30° C.) |

Note
¹⁾The parenthesized value in the column Ps indicates the difference between the temperature at which Ps was measured and the Ch—Sm*C transition temperature, which was measured in the super-cooled state wherein the Sm*C phase is manifested.
²⁾The parenthesized value in the column of the phase transition temperatures indicates the monotropic phase transition temperature.

EXAMPLE 2

Synthesis of

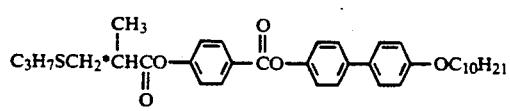

Figure 2:
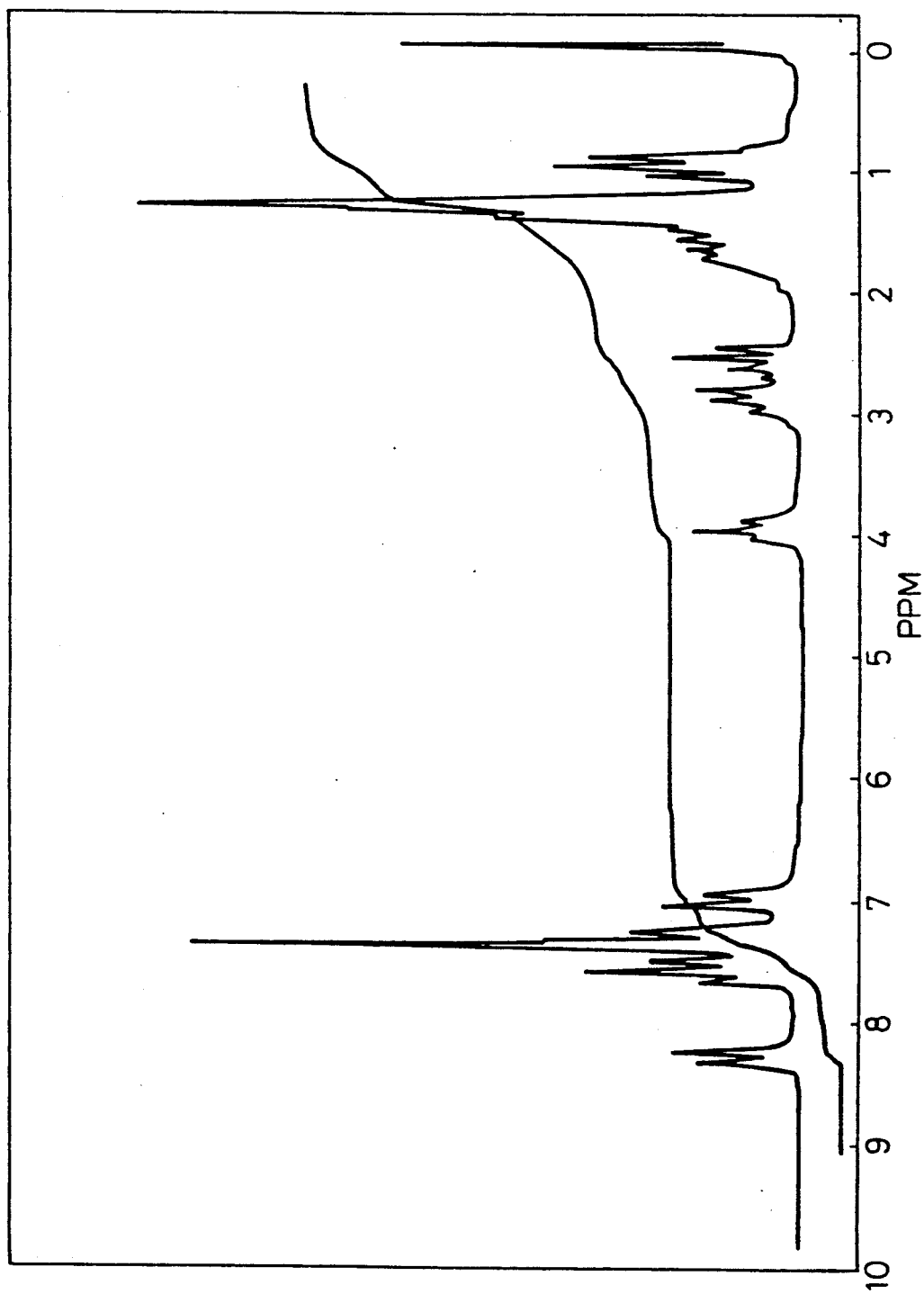
Figure 3:
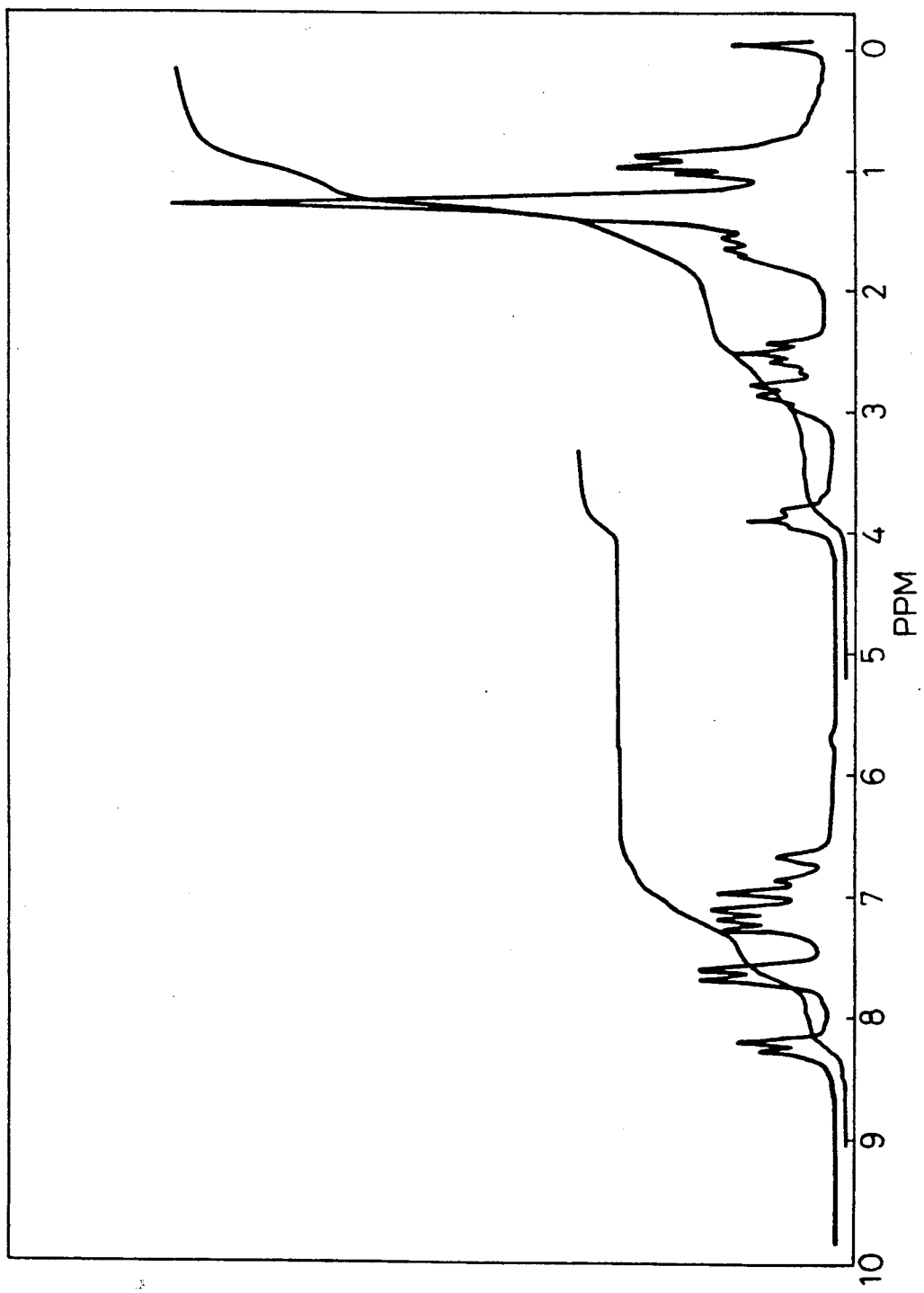

The intended compound was prepared in an amount of 3.34 g in the same manner as described in Example 1 except that 1.62 g of 3-propylthio-2-methylpropionic acid synthesized according to the process of Referential Example 1 was used instead of 1.76 g of 3-butylthio-2- methylpropionic acid and 4.46 g of 4'-n-decyloxybiphenyl 4-(4-hydroxybenzoate) synthesized according to the process of Referential Example 3 was used instead of 4.9 g of 4-n-octyloxyphenyl 4-(4-hydroxybenzoyloxy)benzoate. From the NMR spectrum and the elementary analysis, it was confirmed that the product was the intended compound. The NMR spectrum of the product is shown in FIG. 2. The elementary analysis values were as shown below:

|  | Carbon (%) | Hydrogen (%) | Sulfur (%) |
|---|---|---|---|
| Found values | 73.25 | 7.71 | 5.46 |
| Calculated values | 73.22 | 7.80 | 5.42 | ybenzoyloxy)benzoate. From the NMR spectrum and the elementary analysis, it was confirmed that the product was the intended compound. The NMR spectrum of the compound is shown in FIG. 3. The elementary analysis values were as shown below:

|  | Carbon (%) | Hydrogen (%) | Sulfur (%) |
|---|---|---|---|
| Found values | 73.08 | 7.75 | 5.44 |
| Calculated values | 73.22 | 7.80 | 5.42 |

The phase transition temperature and Ps value of the above compound and a compound synthesized according to the above-mentioned process are shown in Table 3.

TABLE 3

$C_mH_{2m+1}SCH_2{}^*CHCO$—⟨⟩—⟨⟩—$CO$—⟨⟩—$OC_nH_{2n+1}$ (with CH$_3$ and =O substituents)

| m | n | Phase Transition Temperatures (°C.) | Ps (nC/cm$^2$) |
|---|---|---|---|
| 3 | 7 | Cryst ←113.7→ Sm*C ←117.8→ Ch ←125.5→ Iso | 31 (−16° C.) |
| 3 | 10 | Cryst ←99.1→ Sm*C ←100.0→ Ch ←109.6→ Iso | 27 (−28° C.) |

The phase transition temperatures and Ps value of the above compound and compounds prepared according to the above-mentioned process are shown in Table 2.

TABLE 2

$C_mH_{2m+1}SCH_2{}^*CHCO$—⟨⟩—$CO$—⟨⟩—⟨⟩—$OC_nH_{2n+1}$ (with CH$_3$ and =O substituents)

| m | n | Phase Transition Temperature (°C.) | Ps (nC/cm$^2$) |
|---|---|---|---|
| 3 | 7 | Cryst ←95.9→ SmX ←96.3→ Sm*C ←109.1→ Ch ←122.8→ Iso | 36 (−13° C.) |
| 3 | 10 | Cryst —99.6→ Sm*C ←121.4→ Ch ←125.5→ Iso, (65.3)↖SmX↙(85.8) | 37 (−31° C.) |

Note
In Table 2 and the subsequent tables, SmX indicates the unidentified smectic phase.

EXAMPLE 3

Synthesis of

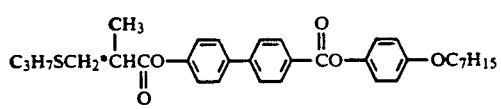

The intended compound was prepared in an amount of 3.20 g in the same manner as described in Example 1 except that 1.62 g of 3-propylthio-2-methylpropionic acid synthesized according to the process of Referential Example 1 was used instead of 1.76 g of 3-butylthio-2-methylpropionic acid and 4.04 g of 4-n-heptyloxyphenyl 4,4'-hydroxybiphenylcarboxylate synthesized according to the process of Referential Example 4 was used instead of 4.9 g of 4-n-octyloxyphenyl 4-(4-hydrox-

EXAMPLE 4

Synthesis of

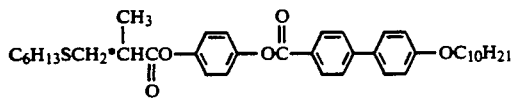

Figure 4:
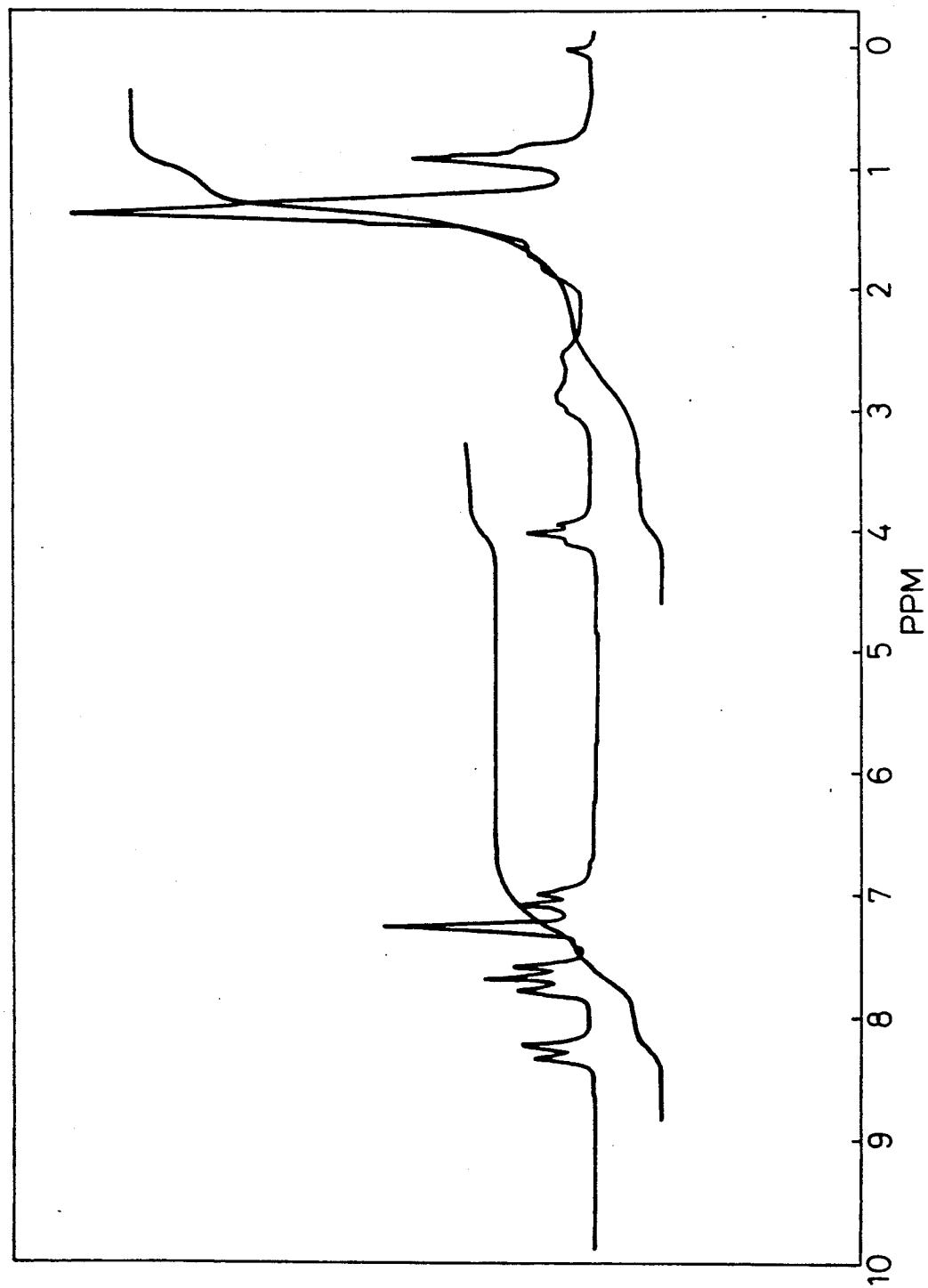

The intended compound was prepared in an amount of 3.69 g in the same manner as descried in Example 1 except that 2.04 g of 3-hexylthiol-2-methylpropionic acid synthesized according to the process of Referential Example 1 was used instead of 1.76 g of 3-butylthio-2-methylpropionic acid and 4.46 g of 4-hydroxyphenyl 4,4'-n-decyloxybiphenylcarboxylate synthesized according to the process of Referential Example 5 was used instead of 4.9 g of 4-n-octyloxyphenyl 4-(4-hydroxybenzoyloxy)benzoate. From the NMR spectrum and the elementary analysis, it was confirmed that the product was the intended compound. The NMR spectrum of the compound is shown in FIG. 4. The elementary analysis values were as follows:

|  | Carbon (%) | Hydrogen (%) | Sulfur (%) |
|---|---|---|---|
| Found values | 74.11 | 8.17 | 5.01 |
| Calculated values | 74.05 | 8.23 | 5.06 |

This compound showed the following phase transition, and the spontaneous polarization at 90° C. (the temperature lower by 30° C. than the temperature of the phase transition of from SmA to Sm*C) was 18 nC/cm² Note, Sm*X₁ and SmX₂ indicate unidentified smectic phases.

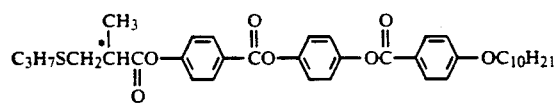

EXAMPLE 5

Synthesis of

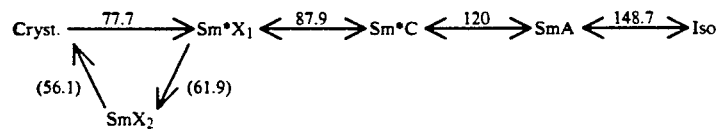

Figure 5:
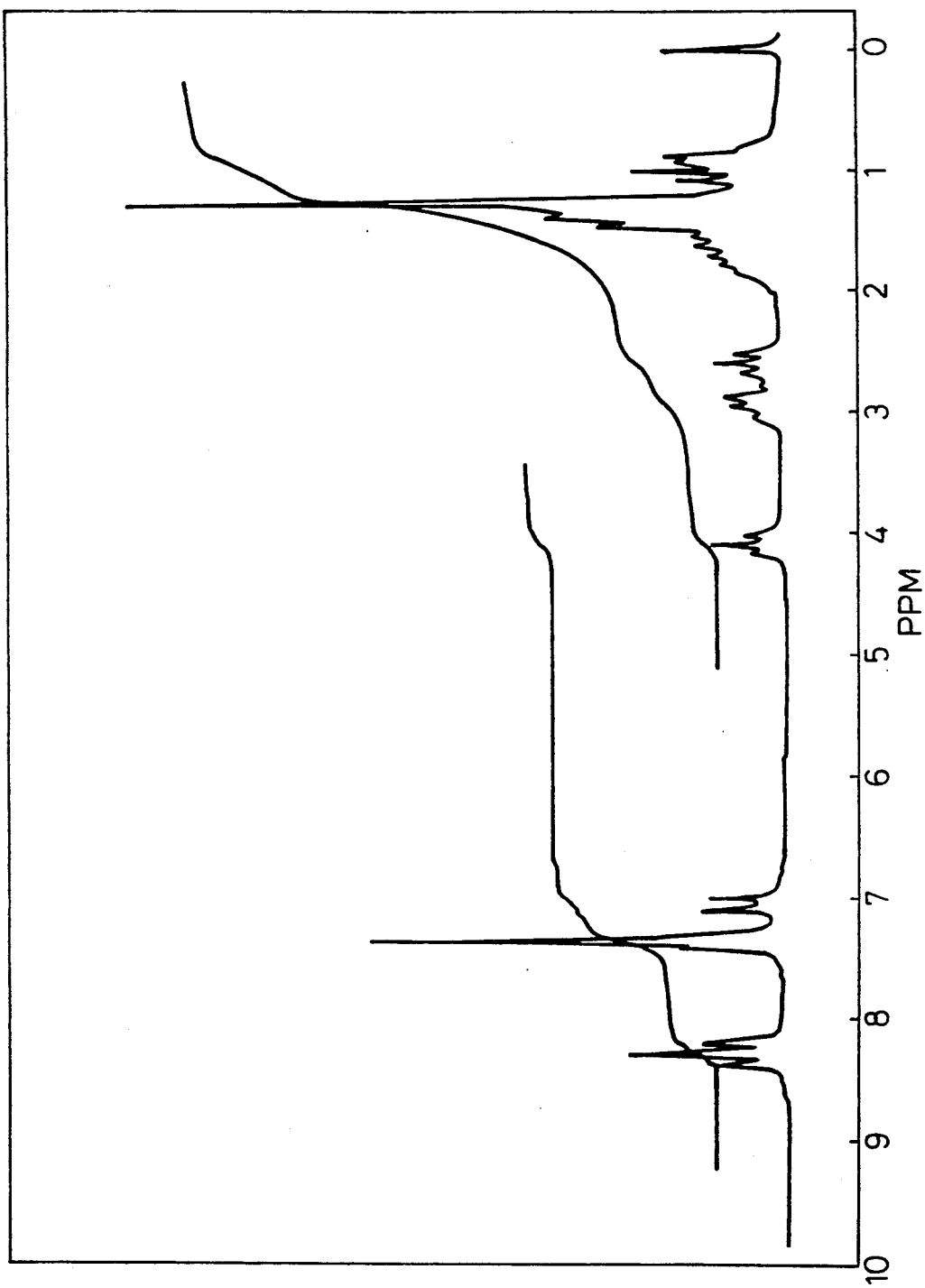

The intended compound was prepared in an amount of 3.85 g in the same manner as described in Example 1 except that 1.62 g of 3-propylthio-2-methylpropionic acid synthesized according to the process disclosed in Referential Example 1 was used instead of 1.76 g of -butylthio-2-methylpropionic acid and 4.90 g of -(4-hydroxybenzoyloxy)phenyl 4-decyloxybenzoate synthesized according to the process of Referential Example 6 was used instead of 4.9 g of 4-n-octyloxyphenyl 4-(4-hydroxybenzoyl)benzoate. From the NMR spectrum and the elementary analysis, it was confirmed that the product was the intended compound. The NMR spectrum of the obtained compound is shown in FIG. 5, and the elementary analysis values were as shown below:

|  | Carbon (%) | Hydrogen (%) | Sulfur (%) |
|---|---|---|---|
| Found value | 70.12 | 7.13 | 5.01 |
| Calculated values | 70.03 | 7.26 | 5.05 |

The compound showed the following phase transition and the spontaneous polarization at about 78° C. (in the supercooled at the temperature lower by 30° C. than the temperature of the phase transition of from Ch to Sm*C) was 29 nC/cm².

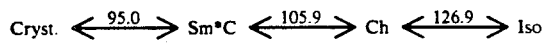

EXAMPLE 6

Synthesis of

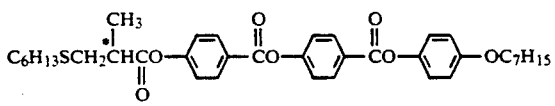

Figure 6:
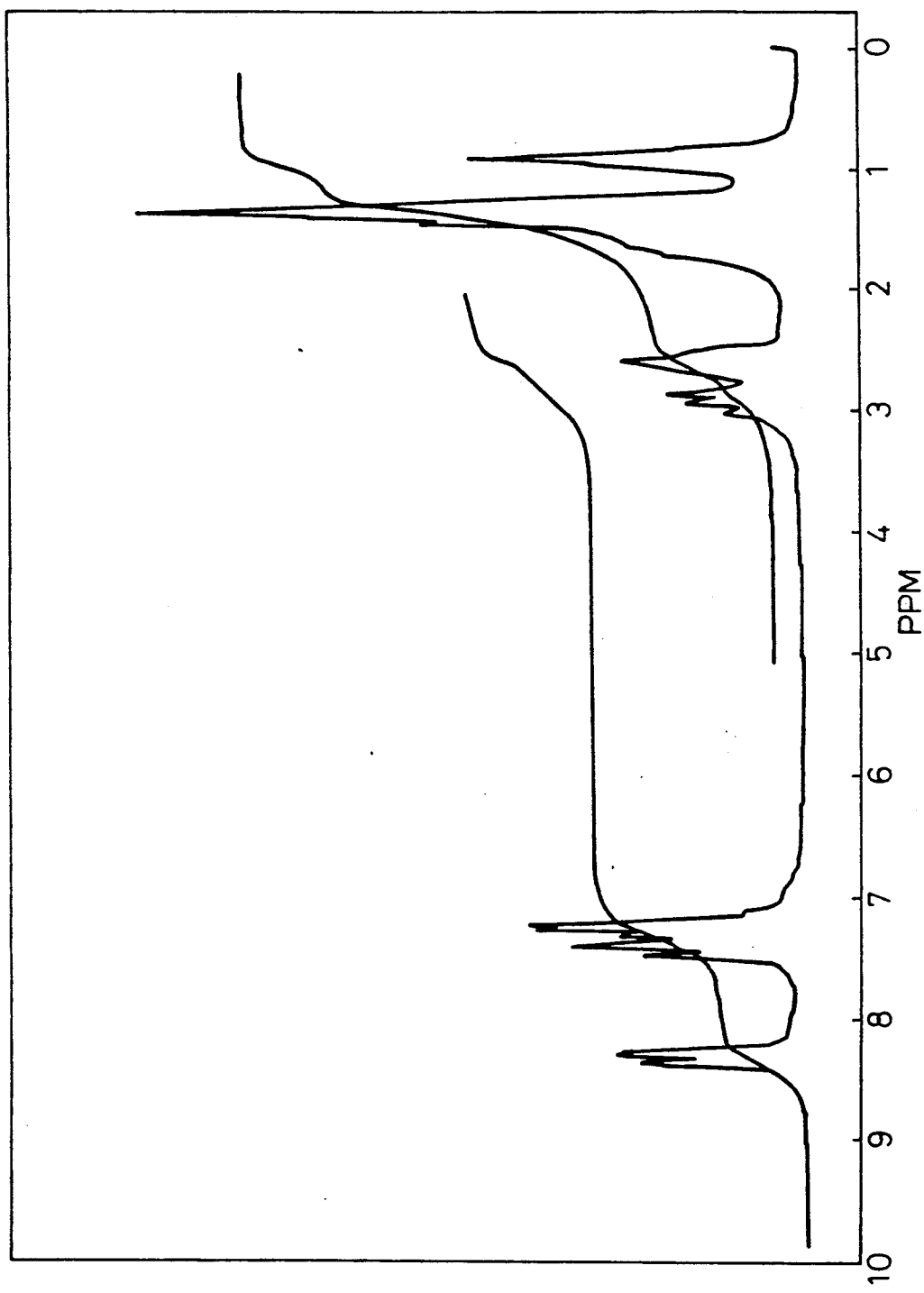

The intended compound was prepared in the same manner as described in Example 1 except that 2.04 g of -hexylthio-2-methylpropionic acid synthesized according to the process of Referential Example 1 was used instead of 1.76 g of 3-butylthio-2-methylpropionic acid and 4.32 g of (4-n-heptyl)phenyl 4-(4-hydroxybenzoyloxy)benzoate was used instead of 4.9 g of 4-n-octyloxyphenyl 4-(4-hydroxybenzoyloxy)benzoate. From the NMR spectrum and the elementary analysis, it was confirmed that the product was the intended compound The NMR spectrum of the obtained compound is shown in FIG. 6, and the elementary analysis values were as shown below:

|  | Carbon (%) | Hydrogen (%) | Sulfur (%) |
|---|---|---|---|
| Found values | 70.12 | 7.13 | 5.01 |
| Calculated values | 70.03 | 7.26 | 5.05 |

The phase transition temperatures of the above compound and a compound prepared according to the above-mentioned process are shown in Table 4.

TABLE 4

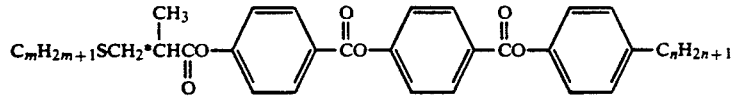

| m | n | Phase Transition Temperatures (°C.) |
|---|---|---|
| 6 | 7 | Cryst ⟶88.6⟶ Ch ⟵94.5⟶ Iso, ↘(75.7)↗ Sm*C |

TABLE 4-continued $C_mH_{2m+1}SCH_2\overset{*}{C}H(CH_3)CO-\text{C}_6H_4-OCO-C_6H_4-CO_2-C_6H_4-C_nH_{2n+1}$

| m | n | Phase Transition Temperatures (°C.) |
|---|---|---|
| 2 | 7 | Cryst $\xrightleftharpoons{82.2}$ Ch $\xrightleftharpoons{117.8}$ Iso <br> ↖ ↙(66.2) <br> Sm*C |

EXAMPLE 7

Synthesis of

Figure 7:
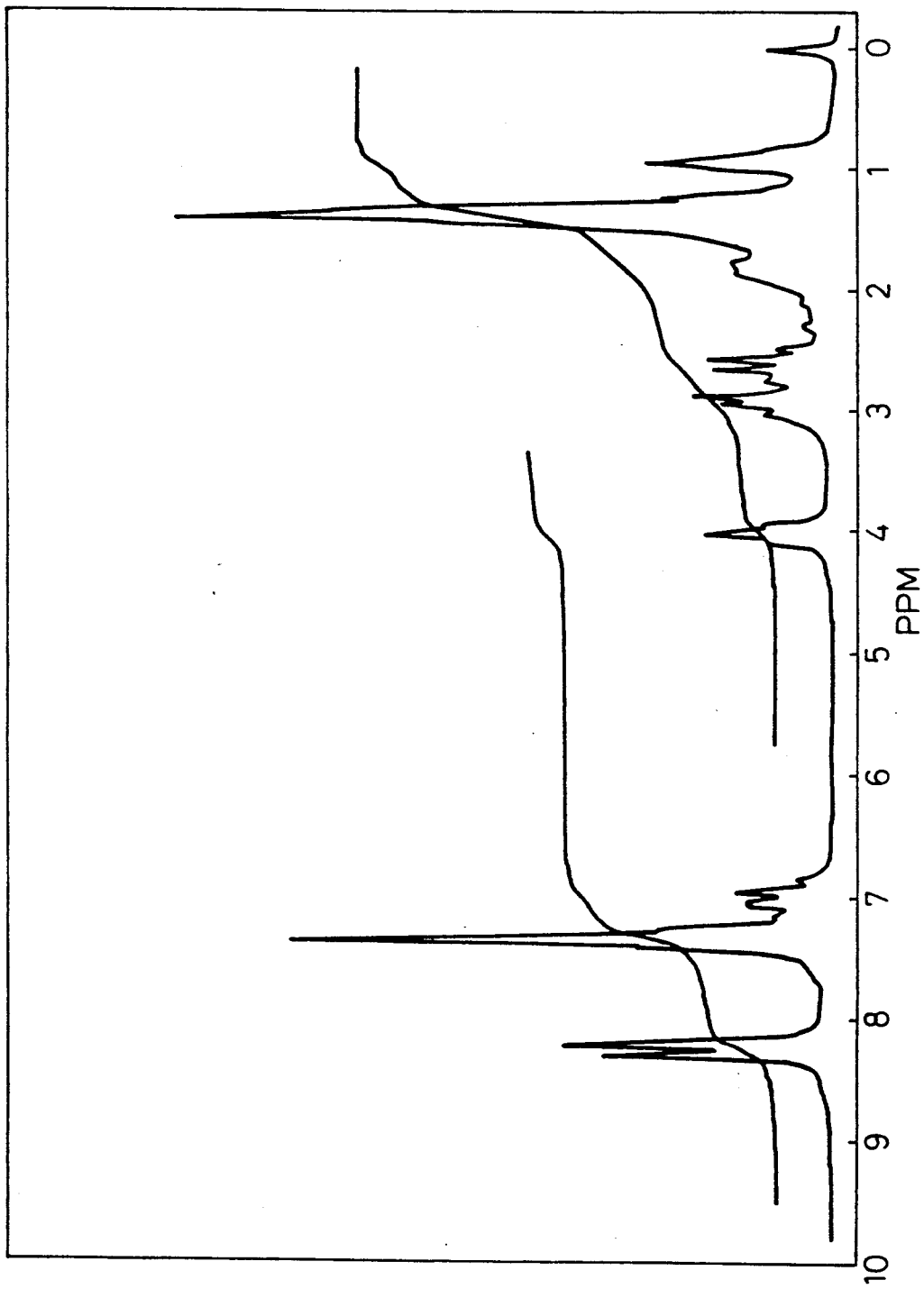

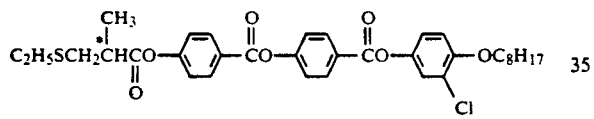

the intended compound. The NMR spectrum of the obtained compound is shown in FIG. 7, and the phase transition temperatures and Ps value of the above compound and a compound prepared according to the above-mentioned process are shown in Table 5.

TABLE 5

$C_mH_{2m+1}SCH_2\overset{*}{C}H(CH_3)CO-\text{C}_6H_4-OCO-C_6H_4-CO_2-C_6H_3(Ck)-OC_nH_{2n+1}$

| m | n | Phase Transition Temperatures (°C.) | Ps (nC/cm²) |
|---|---|---|---|
| 2 | 8 | Cryst $\xrightleftharpoons{54.8}$ Sm*C $\xrightleftharpoons{73.5}$ Ch $\xrightleftharpoons{107.3}$ Iso | 48 (−55° C.) |
| 3 | 8 | Cryst $\xrightleftharpoons{45.2}$ Sm*C $\xrightleftharpoons{87.7}$ Ch $\xrightleftharpoons{92.8}$ Iso | 62 (−50° C.) |

$C_2H_5SCH_2\overset{*}{C}H(CH_3)CO-C_6H_4-OCO-C_6H_4-CO_2-C_6H_3(Cl)-OC_8H_{17}$ In 100 ml of methylene chloride were dissolved 0.15 g of 3-ethylthio-2-methylpropionic acid synthesized according to the process of Referential Example 1 and 0.5 g of the compound synthesized in Referential Example 9, and a solution of 0.3 g of dicyclohexylcarbodiimide in 10 ml of methylene chloride was dropped into the above solution and a reaction was carried out at room temperature with stirring overnight. The reacted solution was washed three times with a 1N aqueous solution of sodium hydrogencarbonate and water, in this order, the organic phase was recovered and dried with anhydrous magnesium sulfate, the organic solvent was evaporated, the product was isolated from the residue by silica gel column chromatography using benzene/n-hexane as eluant and a white powder was obtained. The product was recrystallized from an n-hexane/ethanol mixed solvent to obtain 0.4 g of the intended product. From the NMR spectrum and the elementary analysis, it was confirmed that the product was

EXAMPLE 8

Figure 8:
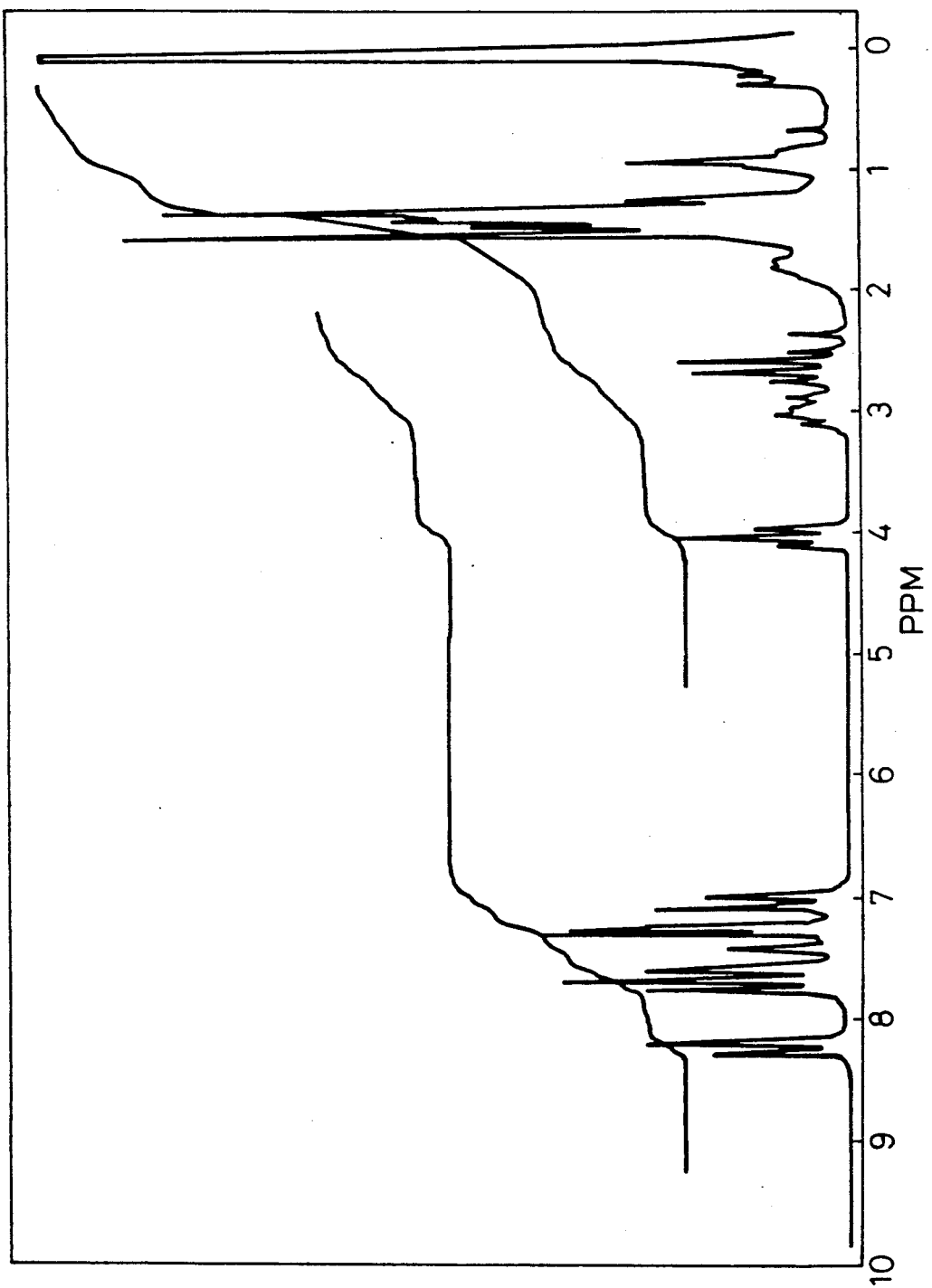

Synthesis of $C_2H_5SCH_2\overset{*}{C}H(CH_3)CO-C_6H_3(Cl)-OC-C_6H_4-C_6H_4-OC_{10}H_{21}$ The intended compound was prepared in the same manner as described in Example 7 except that 1.5 g of 3-ethylthio-2-methylpropionic acid was used and 4.8 g of the compound synthesized in Referential Example 10 was used instead of the compound synthesized in Referential Example 9. From the NMR spectrum, it was confirmed that the obtained product was the intended compound. The NMR spectrum of the obtained compound is shown in FIG. 8.

The phase transition temperatures and Ps value of the compounds obtained from the 2-chloro-substituted and 3-chloro-substituted compounds are shown in Table 6.

TABLE 6

| Substituted Compounds | Phase Transition Temperatures (°C.) | Ps (nC/cm²) |
|---|---|---|
| 3-Cl | Cryst $\xrightleftharpoons{28.9}$ Sm*C $\xrightleftharpoons{96.9}$ SmA $\xrightleftharpoons{141.6}$ Iso | 24 (−70° C.) |
| 2-Cl | Cryst $\xrightleftharpoons{52.6}$ SmA $\xrightleftharpoons{84.9}$ Ch $\xrightleftharpoons{101.4}$ Iso <br> ↖ ↙ <br> (21) Sm*C (28) | 12 (−8° C.) |

EXAMPLE 9

Synthesis of

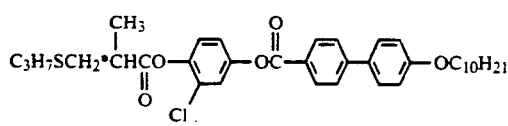

Figure 9:
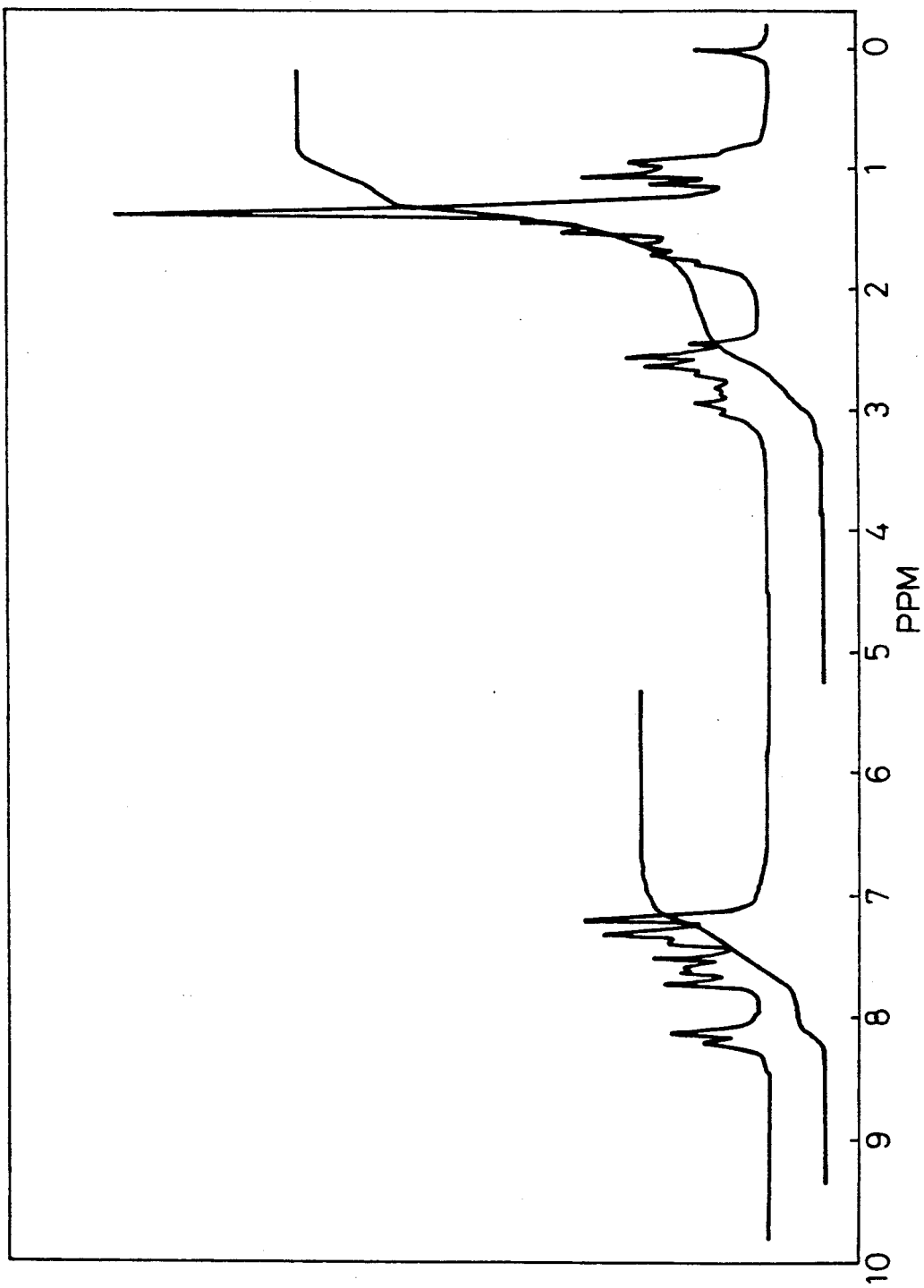

The intended compound was prepared in an amount of 4.1 g in the same manner as described in Example 8 except that 4.7 g of the compound synthesized in Referential Example 11 was used instead of 4.8 g of the compound synthesized in Referential Example 10. From the NMR spectrum, it was confirmed that the obtained product was the intended compound. The NMR spectrum of the obtained compound is shown in FIG. 9. The phase transition temperatures and Ps value of the above compound and a compound synthesized according to the above-mentioned process are shown in Table 7.

TABLE 7

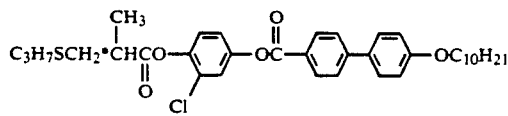

| m | n | Phase Transition Temperatures (°C.) | Ps (nC/cm$^2$) |
|---|---|---|---|
| 3 | 10 | Cryst ←54.4→ Sm*C ←76→ Ch ←99.5→ Iso | 31 (−39° C.) |
| 2 | 10 | Cryst ←47→ Sm*C ←74→ SmA ←109.1→ Iso | 8 (−45° C.) |

EXAMPLE 10

Synthesis of

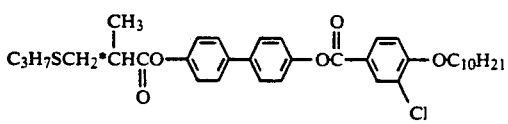

Figure 10:
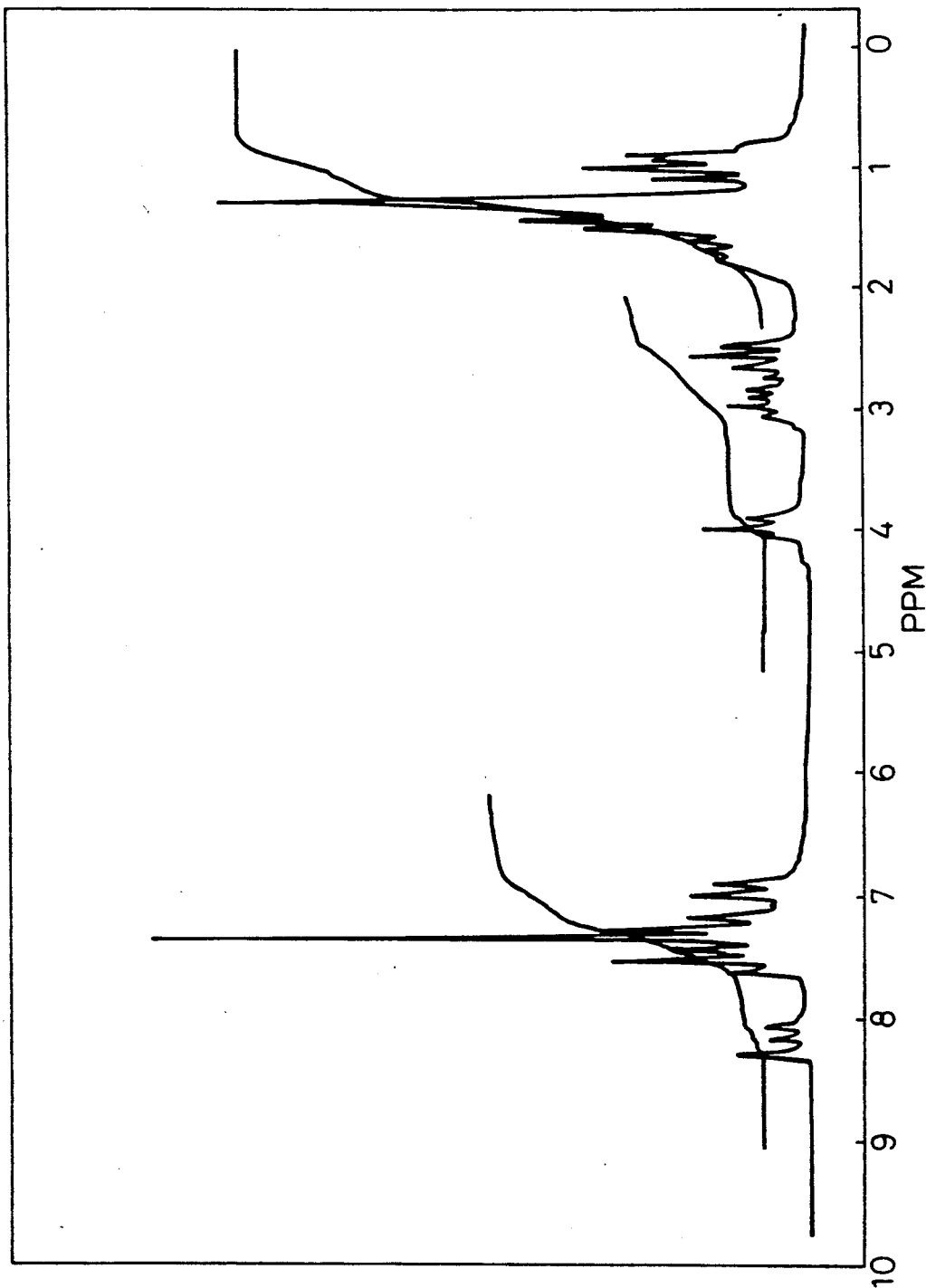

The intended compound was prepared in an amount of 3.9 g in the same manner as described in Example 8 except that 4.8 g of the compound synthesized in Referential Example 12 was used instead of 4.8 g of the compound synthesized in Referential Example 10. From the NMR spectrum, it was confirmed that the obtained product was the intended compound. The NMR spectrum of the obtained compound is shown in FIG. 10. The compound showed the following phase transition, and spontaneous polarization at about 69° C. (the temperature lower by about 26° C. than the transition temperature from the isotropic phase to Sm*C) was 27 nC/cm$^2$.

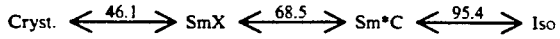

Cryst. ←46.1→ SmX ←68.5→ Sm*C ←95.4→ Iso

EXAMPLE 11

Synthesis of $$C_3H_7SCH_2{}^*\overset{\overset{\displaystyle CH_3}{|}}{C}H\overset{\overset{\displaystyle O}{\|}}{C}O\text{—}\bigcirc\text{—}\bigcirc\text{—}O\overset{\overset{\displaystyle O}{\|}}{C}\text{—}\bigcirc\text{—}OC_{10}H_{21}$$
(with Cl substituent)

Figure 11:
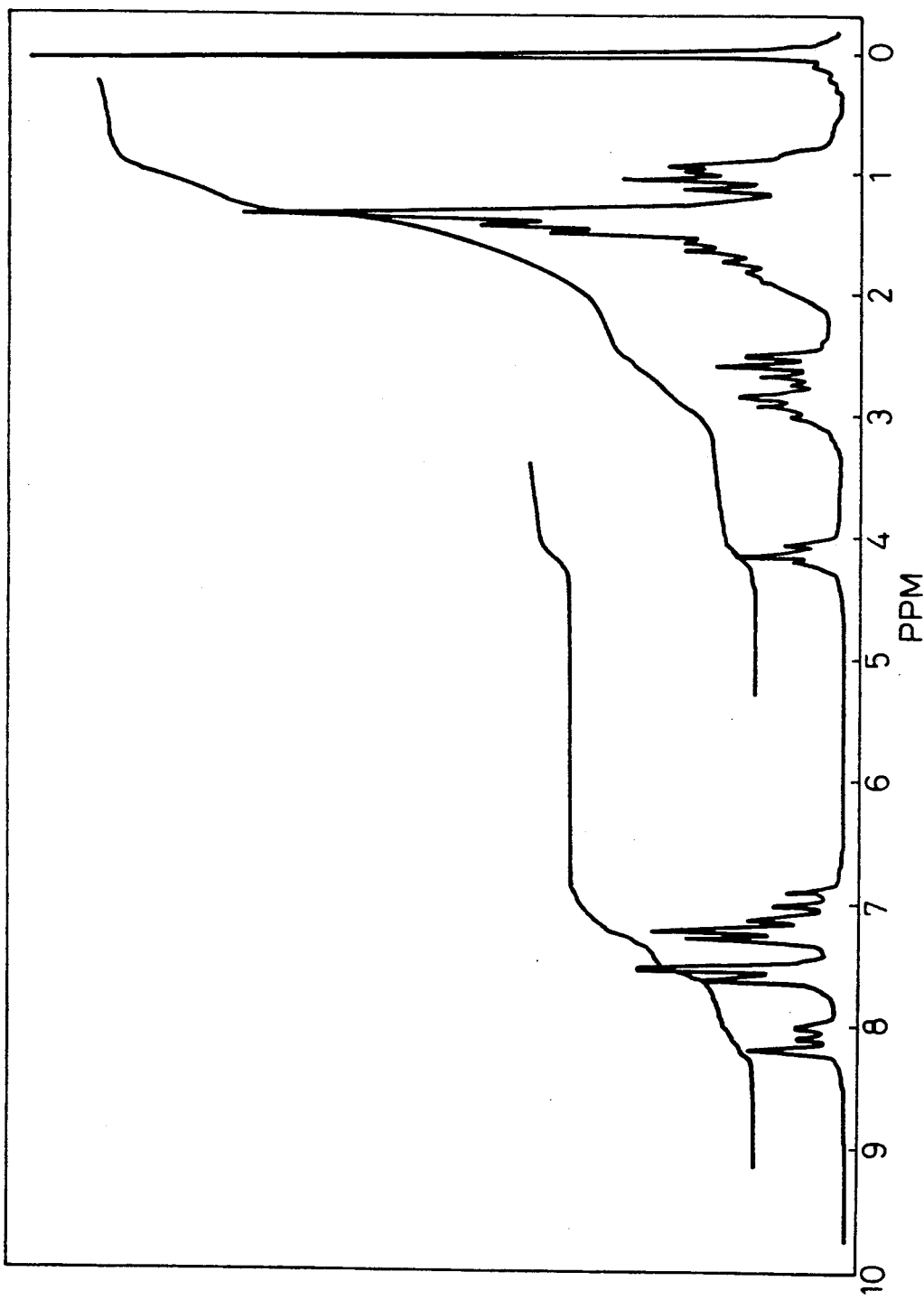

The intended compound was prepared in an amount of 4 g in the same manner as described in Example 8 except that 4.8 g of the compound synthesized in Referential Example 13 was used instead of 4.8 g of the compound synthesized in Referential Example 10. From the NMR spectrum, it was confirmed that the obtained product was the intended compound. The NMR spectrum of the obtained compound is shown in FIG. 11. The phase transition temperatures and Ps value of the above compound and compounds prepared according to the above process are shown in Table 8.

TABLE 8

| m | n | Phase Transition Temperatures (°C.) | Ps (nC/cm$^2$) |
|---|---|---|---|
| 2 | 6 | Cryst ←44→ Sm*C ←92→ Iso | |
| 3 | 6 | Cryst ←57→ Sm*C ←88→ Iso | |
| 2 | 8 | Cryst ←65→ Sm*C ←87→ Iso | |

TABLE 8-continued

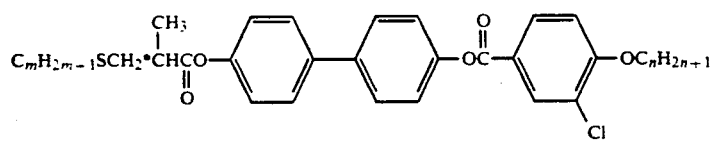

| m | n | Phase Transition Temperatures (°C) | Ps (nC/cm²) |
|---|---|---|---|
| 4 | 8 | Cryst ⇌58⇌ Sm*C ⇌97⇌ Iso | |
| 3 | 10 | Cryst ⇌79⇌ Sm*C ⇌91⇌ Iso | 57 (−35° C.) |

EXAMPLE 12

Figure 12:
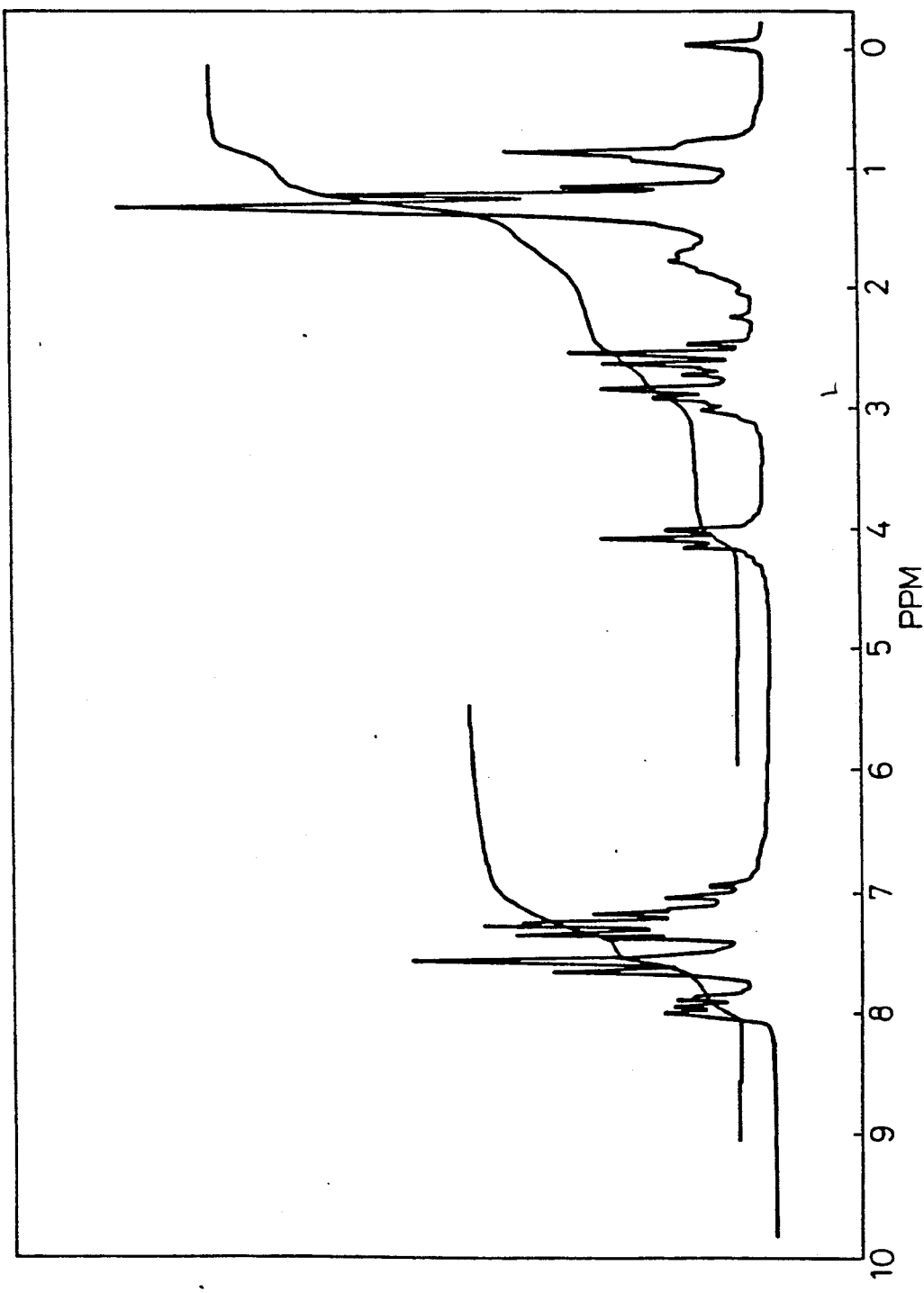

An ester was prepared in an amount of 0.64 g in the same manner as described in Example 7 except that 0.28 g of optically active 3-ethyl-2-methylpropionic acid synthesized in the same manner as described in Referential Example 1 and 0.82 g of 4'-hydroxybiphenyl -fluoro-4-hexyloxybenzoate synthesized in the same manner as described in Referential Example 13 were used. The structure of the compound was confirmed by the NMR spectrum. The NMR spectrum of the obtained compound is shown in FIG. 12. The phase transition temperatures of the obtained compound and a compound synthesized according to the above-mentioned process are shown in Table 9.

TABLE 9

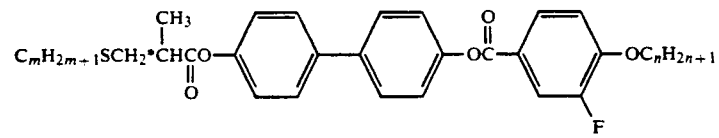

| m | n | Phase Transition Temperatures (°C) |
|---|---|---|
| 3 | 6 | Cryst ⇌81⇌ Sm*C ⇌114⇌ Ch ⇌135⇌ Iso |
| 3 | 8 | Cryst ⇌85⇌ Sm*C ⇌116⇌ Ch ⇌121⇌ Iso |

TABLE 10

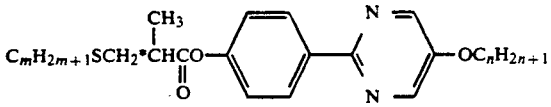

| m | n | Phase Transition Temperatures (°C) |
|---|---|---|
| 4 | 6 | Cryst ⇌54⇌ Iso |
| 2 | 8 | Cryst ⇌62⇌ Iso |
| 5 | 10 | Cryst ⇌53⇌ Iso |
| 6 | 10 | Cryst ⇌49⇌ Iso |

EXAMPLE 13

Figure 13:
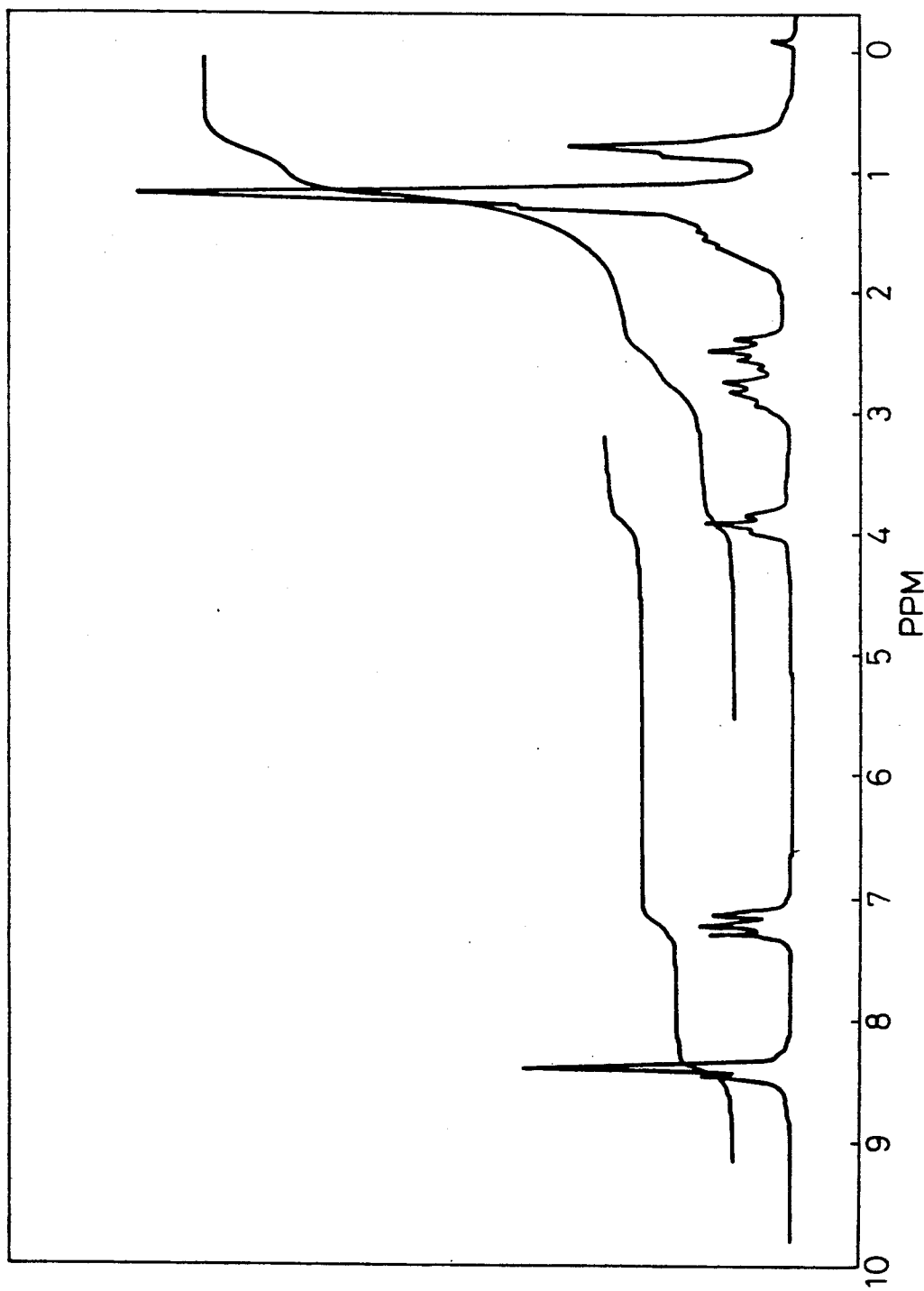

An ester was prepared in an amount of 0.75 g in the same manner as described in Example 1 except that 0.67 g of optically active 3-butylthio-2-methylpropionic acid, 0.876 g of 5-n-octyloxy-2-(p-hydroxyphenyl)-pyrimidine (FK-1125-08 supplied by Teikoku Kagaku Sangyo) and 0.83 g of dicyclohexylcarbodiimide were used. The structure of the compound was confirmed by the NMR spectrum. The NMR spectrum of the obtained compound is shown in FIG. 13. The phase transition temperatures of the above compound and compounds of the same kind synthesized according to the above process are shown in Table 10.

EXAMPLE 14

In 30 ml of water was dissolved 6 g of sodium hydroxide, 30 ml of ethanol was added to the solution, 6.7 g of methyl L-(+)-3-acetylthio-2-methylpropionate was added to the mixture, stirring was conducted at room temperature for 1 hour, 14.2 g of 1-bromo-3,3,3-trifluoropropane was added, and the mixture was stirred at room temperature overnight to effect reaction. Then the reacted mixture was neutralized with hydrochloric acid and extracted with diethyl ether, and the extract was washed three times with 1N hydrochloric acid and water. The organic phase was recovered and dried on anhydrous magnesium sulfate, and the organic solvent was evaporated to obtain 5.2 g of optically active 3-(3,3,3-trifluoropropyl)thio-2-methylpropionic acid.

Then, 2.16 g of the obtained compound and 4.9 g of 4-decyloxyphenyloxycarbonylphenyl 4-hydroxybenzoate synthesized according to the process of Referential Example 2 were dissolved in 100 ml of methylene chloride, a solution of 2.26 g of dicyclohexylcarbodiimide in 10 ml of methylene chloride was dropped into the above solution, the mixture was stirred at room temperature overnight to effect a reaction, the reacted mixture was washed three times with a 1N aqueous solution of sodium hydrogencarbonate and water in this order, the organic phase was recovered and dried with anhydrous magnesium sulfate, the organic solvent was evaporated, .the reaction product was isolated from the residue by silica gel column chromatography using benzene/hexane as eluant, and a white powder was obtained. The obtained product was recrystallized from an n-hexane/ethanol mixed solvent to obtain 4.7 g of a purified product. From the NMR spectrum and the elementary analysis, it was confirmed that the product was the intended compound.

The phase transition temperatures (° C.) of the obtained compounds were as shown below.

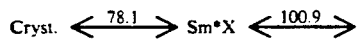

EXAMPLE 15

Synthesis of

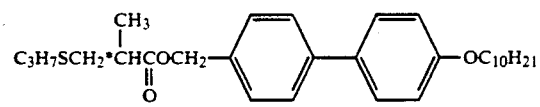

In 100 ml of methylene chloride were dissolved 1.62 g of 3-propylthio-2-methylpropionic acid synthesized according to the process of Referential Example 1 and 3.4 g of 4-hydroxymethyl-4'-decyloxybiphenyl (FK-1122-010 supplied by Teikoku Kagaku Sangyo), and a solution of 2.26 g of dicyclohexylcarbodiimide in 10 ml of methylene chloride was dropped into the above solution and the mixture was stirred at room temperature overnight to effect reaction. Then the reacted mixture was washed three times with a 1N aqueous solution of sodium hydrogencarbonate and water in this order, the organic phase was recovered, the reaction product was isolated from the residue by silica gel column chromatography using a benzene/n-hexane mixed solvent as eluant, and a white powder was obtained The product was recrystallized from an n-hexane/ethanol mixed solvent to obtain 4.7 g of the intended compound From the elementary analysis and the NMR spectrum, it was confirmed that the product was the intended compound The phase transition temperature (° C.) of the obtained compound was as shown below.

$$Cryst. \xleftrightarrow{22} Iso$$

EXAMPLE 16

Figure 14:
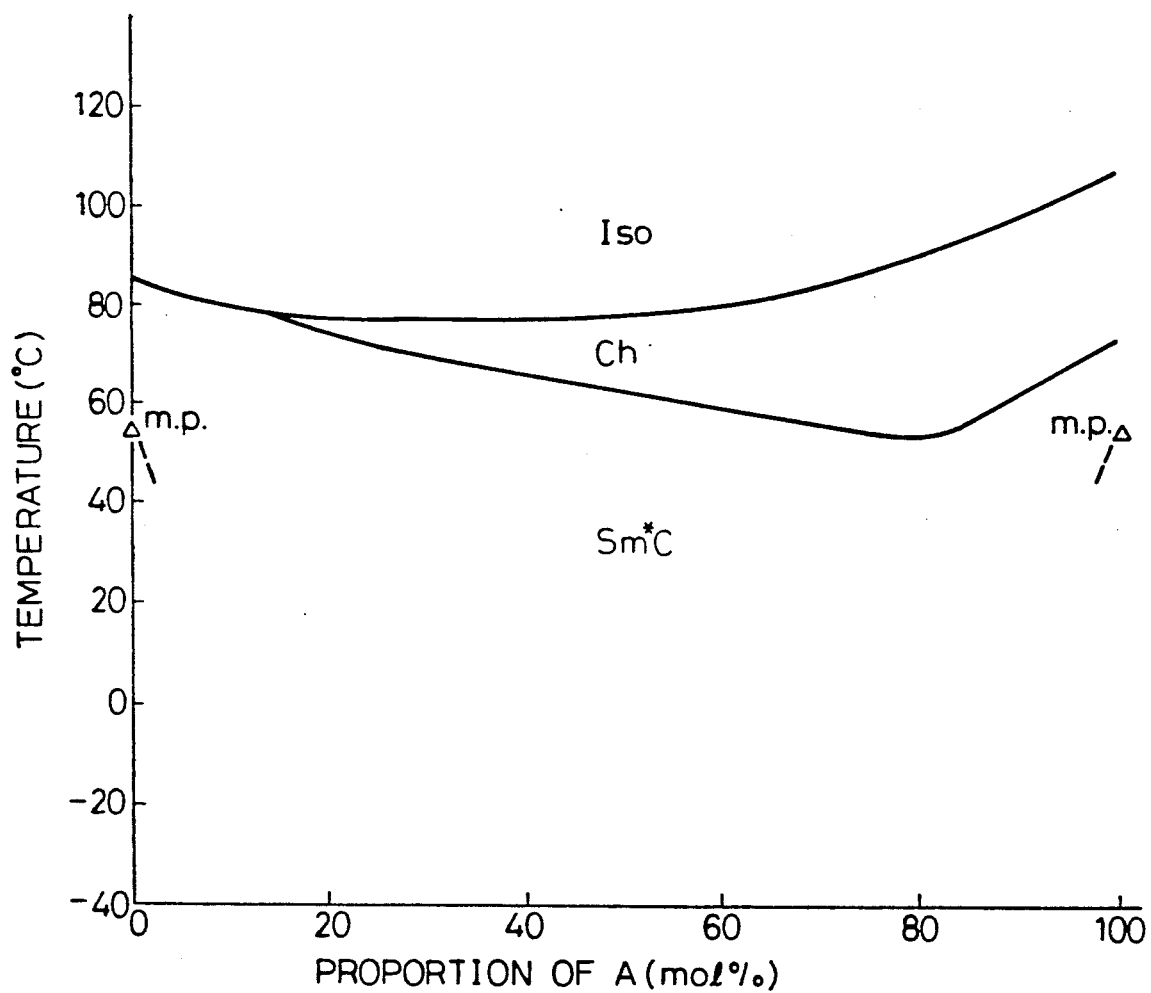
FIGS. 14 and 15 illustrate phase diagrams of liquid crystal compositions prepared in Examples 16 and 17, respectively.

The compound (A) synthesized in Example 7 and represented by the following formula:

$C_2H_5SCH_2{}^*CHCO$—⟨⟩—$\overset{O}{\underset{\|}{CO}}$—⟨⟩—$\overset{O}{\underset{\|}{CO}}$—⟨⟩—$OC_8H_{17}$
with $CH_3$ branch and $Cl$ was mixed the compound (B) synthesized according to the process of Example 11 (m=6, n=3) and represented by the following formula:

$C_6H_{13}O$—⟨⟩—$\overset{O}{\underset{\|}{CO}}$—⟨⟩—⟨⟩—$O\overset{O}{\underset{\|}{C}}{}^*CHCH_2SC_3H_7$
with $Cl$ and $CH_3$ and the phase diagram of the mixture was examined. The obtained results are shown in FIG. 14. The temperature range showing the Sm*C phase was greatly expanded on the lower temperature side, and surprisingly, an optical response was observed even at −20° C. by application of an electric field. When the composition was stored at −12° C. for one week, no crystallization occurred and an optical response was still observed upon application of an electric field.

EXAMPLE 17

Figure 15:
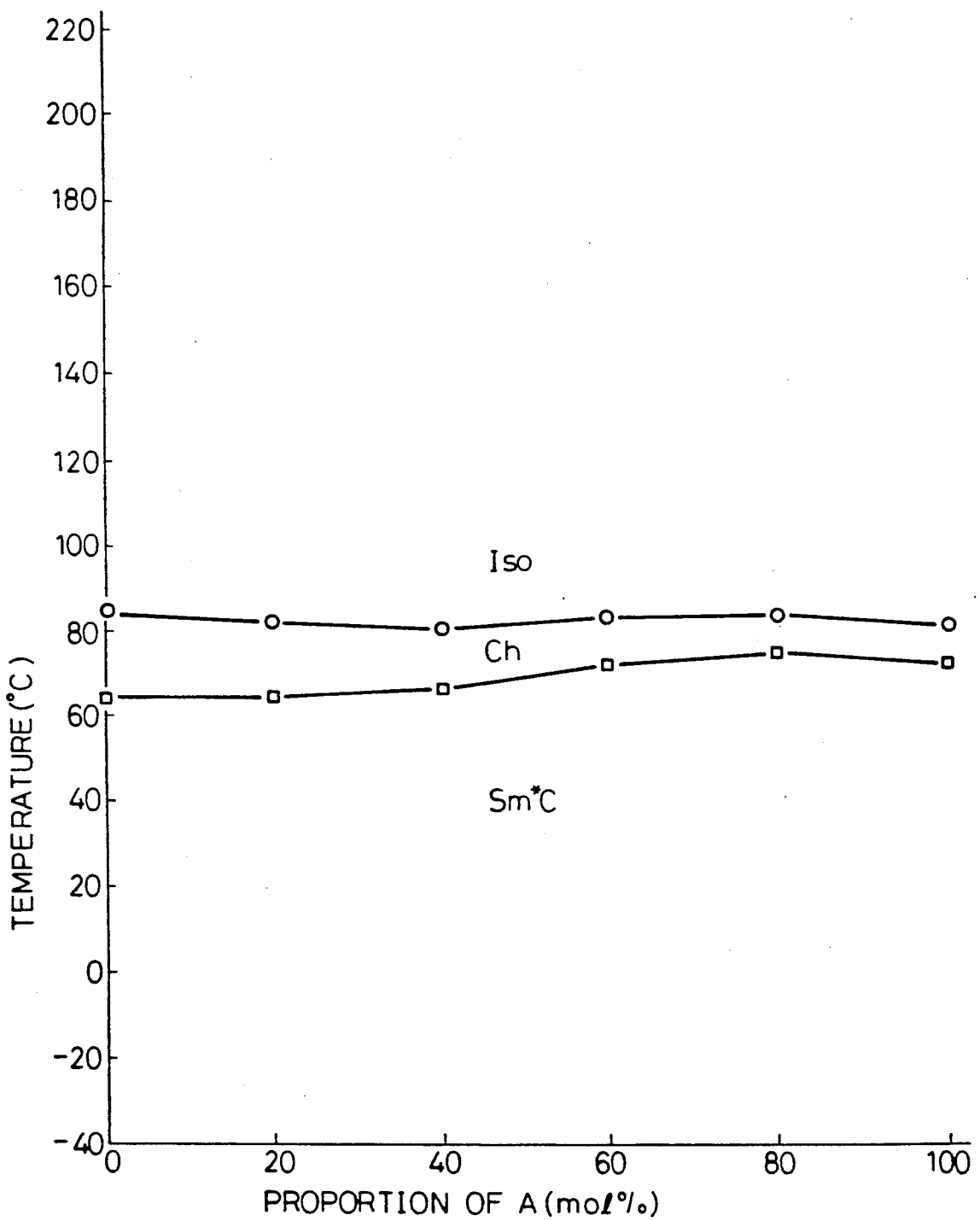

The following two mixtures A and B were prepared and mixed, and the phase diagram was examined. The obtained results are shown in FIG. 15. Surprisingly, crystallization did not occur even at −40° C. in any composition, and compositions having a broad Sm*C phase were obtained.

A:

$C_6H_{13}SCH_2{}^*CHCO$—⟨⟩—$CO$—⟨⟩—$CO$—⟨⟩—$OC_8H_{17}$    50 mol % and

B:

$C_2H_5SCH_2{}^*CHCO$—⟨⟩—⟨⟩—$OC$—⟨⟩—$OC_8H_{17}$    50 mol %

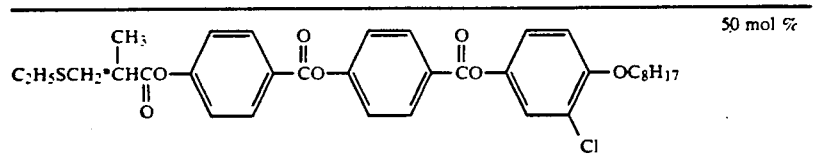

50 mol % and

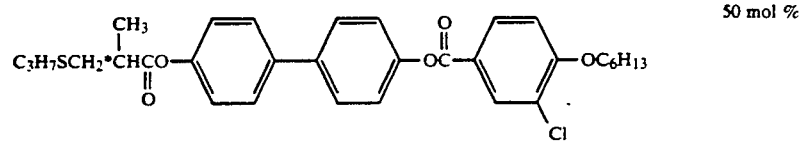

50 mol %

EXAMPLE 18

When 5 parts of the compound synthesized in Example 13, which showed no liquid crystal property, were mixed with 95 parts of the liquid crystal mixture prepared in Referential Example 14, which showed no optical activity, a ferroelectric liquid crystal mixture was obtained. The phase transition temperatures (° C) of the composition were as shown below.

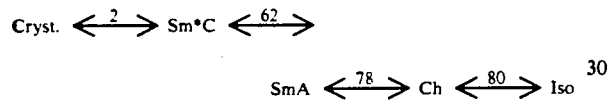

When a liquid crystal element was fabricated by using a polyimide film for the alignment layer while adjusting the cell gap to 2 μm and the tilt angle was measured, it was found that the tilt angle was 10° and the bistability was good.

EXAMPLE 19

When 20 parts of the compound synthesized in Example 13, which showed no liquid crystal property, were mixed with 80 parts of the liquid crystal mixture prepared in Referential Example 14, which showed no optical activity, a ferroelectric liquid crystal was obtained. The phase transition temperatures (° C.) of the composition were as shown below.

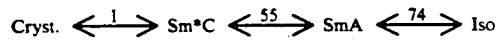

When a square-wave of $V_{p-p}$ (the voltage difference between the peaks) was applied, the response time (the time required for the light transmission to change to 50% from 0% after the application of the square-wave) was 265 μsec.

EXAMPLE 20

A ferroelectric liquid crystal composition was prepared by mixing 40 parts of the compound synthesized in Example 13, which showed no liquid crystal property, with 60 parts of the mixture synthesized in Referential Example 14, which showed no optical activity. The phase transition temperatures (° C.) of the composition were as shown below.

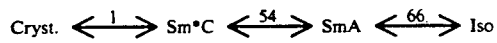

The response time was 90 μsec when $V_{p-p}$ was 20 V.

EXAMPLE 21

The phase temperatures of compositions prepared by mixing a ferroelectric liquid crystal composition A comprising the following compounds at the following mixing ratio with the liquid crystal mixture B prepared in Referential Example 14 at a predetermined mixing ratio are shown in Table 11.

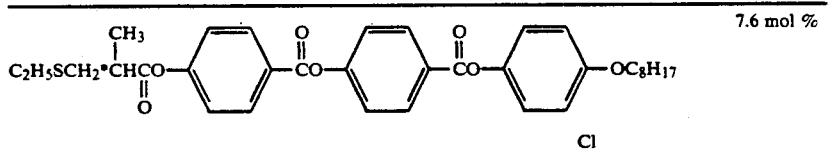

7.6 mol %

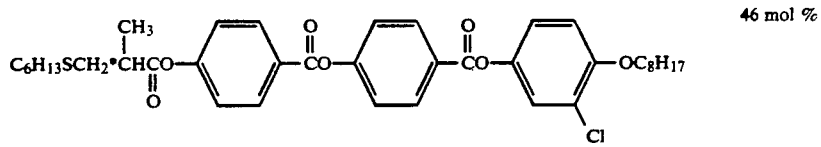

46 mol %

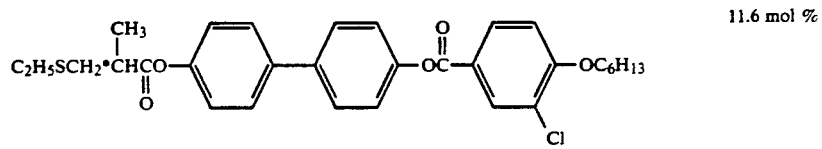

11.6 mol %

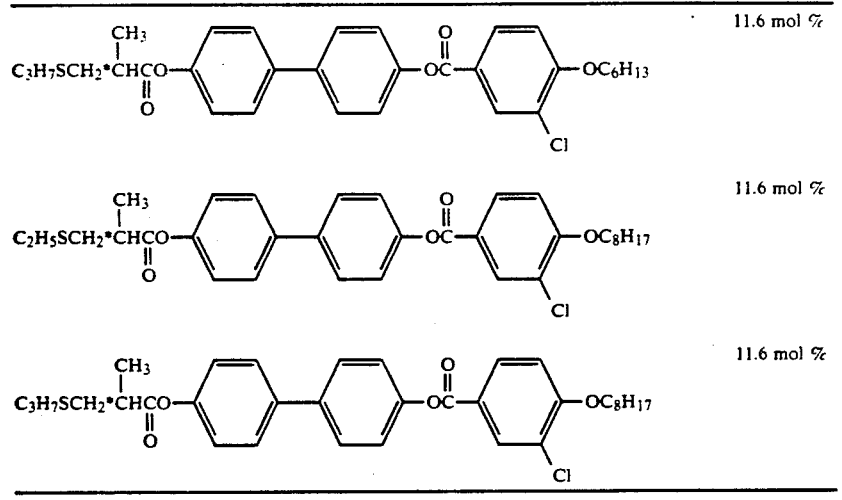

11.6 mol %

11.6 mol %

11.6 mol %

TABLE 11

| A:B Mixing Ratio | Phase Transition Temperatures (°C.) |
|---|---|
| 2:98 | Cryst. ←1→ Sm*C ←62→ SmA ←67→ Ch ←77→ Iso |
| 5:95 | Cryst. ←1→ Sm*C ←63→ SmA ←69→ Ch ←75→ Iso |
| 10:90 | Cryst. ←1→ Sm*C ←64→ Ch ←73→ Iso |
| 20:80 | Cryst. ←-3→ Sm*C ←59→ Ch ←72→ Iso |
| 40:60 | Cryst. ←-20→ Sm*C ←56→ Ch ←68→ Iso |
| 60:40 | Cryst. ←≤-20→ Sm*C ←55→ Ch ←69→ Iso |
| 80:20 | Cryst. ←≤-20→ Sm*C ←60→ Ch ←70→ Iso |

The compound of the present invention, which shows a liquid crystalline property, provides an excellent performance. For example, the compound has a high spontaneous polarization as the ferroelectric liquid crystal composition, the temperature range showing the ferroelectric property is wide, a liquid crystal composition comprising this compound has an Sm*C phase-showing temperature range greatly expanded on the lower temperature side, any other smectic phase is not shown at temperatures lower than the Sm*C phase-showing temperature range, coloration does not occur, the chemical stability such as the resistance to the hydrolysis is high, and the light stability is excellent. The compound of the present invention, which does not show a ferroelectric property, has excellent performances such that, when the compound is used as an additive component to a ferroelectric liquid crystal, the spontaneous polarization of the composition is increased, the temperature range in which liquid crystalline property is manifested is expanded, the response time is shorten, coloration does not occur, and the chemical stability or the light stability is not lowered. A liquid crystal composition comprising at least one of these compounds has the above-mentioned characteristics, and thus the composition is practically valuable.

We claim:

1. A method for widening the temperature range of the liquid crystal phase of a liquid crystal comprising incorporating at least one optically active compound represented by the general formula (1):

$$R_1SCH_2\overset{*}{C}HCO-A-R_2 \quad (1)$$
$$\underset{\text{CH}_3}{\overset{}{|}} \quad \underset{O}{\overset{\|}{}}$$

wherein A stands for 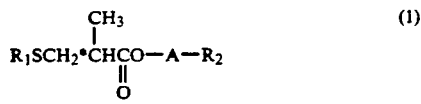,

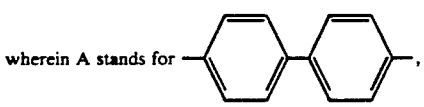

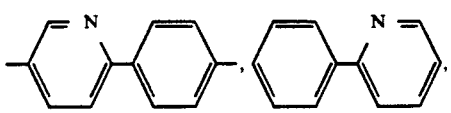

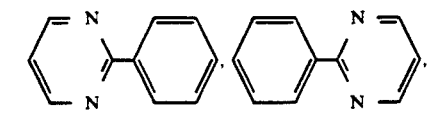

-continued

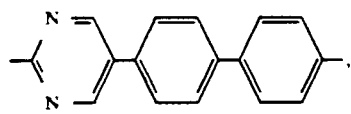

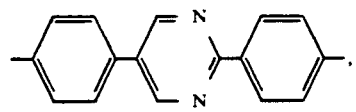

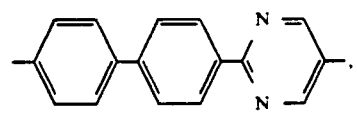

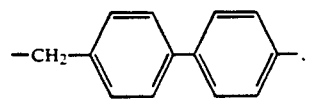

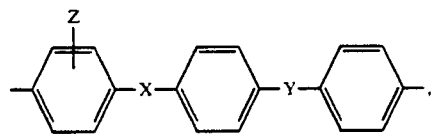

-continued

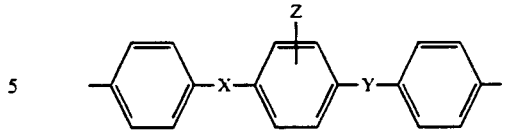

or

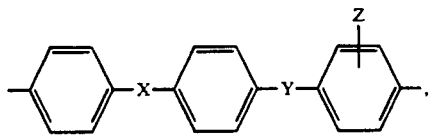

X and Y independently stand for $-\overset{O}{\underset{\|}{C}}O-$, $-O\overset{O}{\underset{\|}{C}}-$ or a single bond, Z stands for a hydrogen atom, a halogen atom or a cyano group, $R_1$ stands for an alky group or fluoroalkyl group having 1 to 18 carbon atoms, $R_2$ stands for an alkyl group or alkoxy group having 1 to 18 carbon atoms, and *C stands for the asymmetric carbon atom;

with 1-90 mol% of a non-chiral liquid crystal having a phase system of isotropic phase-nematic phase-smectic A phase-smectic C phase or isotropic-nematic phase-smectic C phase or a mixture thereof within a range not destroying the liquid crystal property.

* * * * *